(12) United States Patent
Komatsubara et al.

(10) Patent No.: US 9,259,365 B2
(45) Date of Patent: Feb. 16, 2016

(54) ABSORBENT ARTICLE PACKAGE

(75) Inventors: Daisuke Komatsubara, Kagawa (JP); Takeshi Ikegami, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 113 days.

(21) Appl. No.: 14/123,196

(22) PCT Filed: Jun. 1, 2012

(86) PCT No.: PCT/JP2012/003641
§ 371 (c)(1),
(2), (4) Date: Nov. 29, 2013

(87) PCT Pub. No.: WO2012/164963
PCT Pub. Date: Dec. 6, 2012

(65) Prior Publication Data
US 2014/0131248 A1    May 15, 2014

(30) Foreign Application Priority Data

Jun. 2, 2011    (JP) ................................ 2011-124670

(51) Int. Cl.
| | | |
|---|---|---|
| *B65D 85/16* | (2006.01) | |
| *B65D 65/28* | (2006.01) | |
| *A61F 13/551* | (2006.01) | |
| *B65D 69/00* | (2006.01) | |
| *B65D 83/08* | (2006.01) | |

(52) U.S. Cl.
CPC .......... *A61F 13/55115* (2013.01); *B65D 69/00* (2013.01); *B65D 83/0835* (2013.01)

(58) Field of Classification Search
CPC .... B65D 75/5833; B65D 85/16; B65D 75/54; A61F 13/55115; A61F 13/5511; A61F 13/551; A61F 5/4401

USPC ........... 206/440, 494; 383/207, 209, 120, 10, 383/66, 200; 604/357
See application file for complete search history.

(56) References Cited

U.S. PATENT DOCUMENTS 4,770,298 A * 9/1988 McFarland et al. ........... 206/390
4,966,286 A * 10/1990 Muckenfuhs ................. 206/494
(Continued)

FOREIGN PATENT DOCUMENTS

EP    0778015 A1    11/1997
EP    1118568 A2    7/2001
(Continued)

OTHER PUBLICATIONS

International Search Report corresponding to PCT/JP2012/003641, dated Aug. 28, 2012.
(Continued)

*Primary Examiner* — Chun Cheung
(74) *Attorney, Agent, or Firm* — Hauptman Ham, LLP

(57) ABSTRACT

An absorbent article package, includes: a plurality of absorbent articles each folded to define a first outer face and a second outer face; and a packing bag that stores the plurality of absorbent articles in a layered state such that the first outer face of each of the plurality of absorbent articles makes contact with the second outer face of an adjacent absorbent article, in which each absorbent article includes an engagement member arranged on the first outer face thereof and engaging with the second outer face of the adjacent absorbent article, and the packing bag includes a first face positioned to face the first or second outer faces of the absorbent articles stored in the packing bag and configured to form therein an opening to allow the absorbent articles to be extracted.

13 Claims, 22 Drawing Sheets

(56) References Cited

U.S. PATENT DOCUMENTS

| | | |
|---|---|---|
| 5,050,742 A | 9/1991 | Muckenfuhs |
| 2004/0064122 A1 | 4/2004 | Hansson |
| 2004/0129592 A1* | 7/2004 | Otsubo ......................... 206/440 |
| 2006/0074390 A1* | 4/2006 | Price et al. .................... 604/357 |

FOREIGN PATENT DOCUMENTS

| | | |
|---|---|---|
| JP | 6-511451 A | 12/1994 |
| JP | 2006256654 A | 9/2006 |
| JP | 2008222261 A | 9/2008 |
| WO | 92/07773 A1 | 5/1992 |
| WO | 2005063596 A1 | 7/2005 |

OTHER PUBLICATIONS

Extended European Search Report dated Oct. 7, 2014, corresponding to European patent application No. 12793829.8.

Office Action mailed Jun. 2, 2015, corresponding to Japanese patent application No. 2011-124670.

\* cited by examiner

ABSORBENT ARTICLE PACKAGE

RELATED APPLICATIONS

The present application is a National Phase of International Application Number PCT/JP2012/003641, filed Jun. 1, 2012, and claims priority from Japanese Application Number 2011-124670, filed Jun. 2, 2011.

TECHNICAL FIELD

The present disclosure relates to an absorbent article package.

BACKGROUND ART

In the related art, absorbent articles, such as disposable diapers, are commercially supplied as an absorbent article package including a plurality of absorbent articles and a packing bag for storing a plurality of absorbent articles. More specifically, the plurality of absorbent articles are stacked while they are folded in a flat shape, and the plurality of the stacked absorbent articles are compressed into the packing bag to provide a package.

Such an absorbent article package has a tearable portion, such as a perforated line, formed in a predetermined area of the packing bag, and an opening for extracting the absorbent article is formed by tearing the tearable portion. In addition, the plurality of absorbent articles stored in the packing bag are extracted one by one from the opening for use.

The inventor(s) has noted that, in the above described absorbent article package, the absorbent article can be easily extracted from the opening only when the number of absorbent articles stored in the packing bag is large, because one or more absorbent articles are located in the vicinity of this opening. However, the absorbent articles remaining in the packing bag are located far from the opening (deep inside the packing bag) when the number of absorbent articles stored in the packing bag is reduced. For this reason, in order to extract the remaining absorbent articles stored in the packing bag, it is necessary to put the hand inside the packing bag through the opening. Therefore, it is sometimes difficult to extract the absorbent article from the packing bag.

SUMMARY OF INVENTION

According to some embodiments of the present invention, an absorbent article package, includes: a plurality of absorbent articles each folded to define a first outer face and a second outer face; and a packing bag that stores the plurality of absorbent articles in a layered state such that the first outer face of each of the plurality of the absorbent articles makes contact with the second outer face of an adjacent absorbent article. Each absorbent article includes an engagement member arranged on the first outer face thereof and engaging with the second outer face of the adjacent absorbent article. The packing bag includes a first face positioned to face the first or second outer faces of the absorbent articles stored in the packing bag and configured to form therein an opening to allow the absorbent articles to be extracted.

DESCRIPTION OF EMBODIMENTS

Hereinafter, an absorbent article package according to a preferable embodiment will be described with reference to the drawings. In each of the following embodiments, a package 1 obtained by packing pet absorbent articles 10 as an absorbent article will be described.

Figure 1:
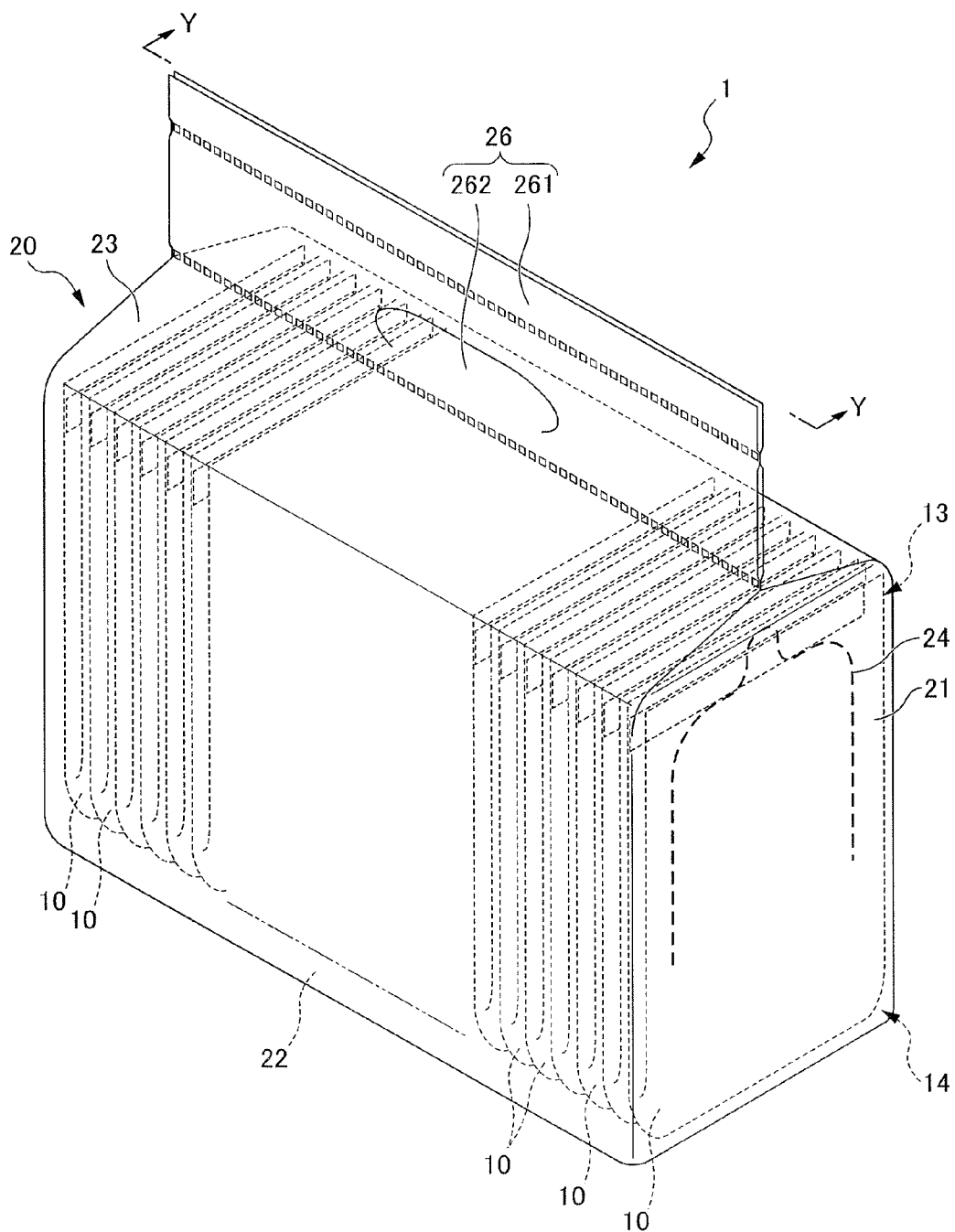
FIG. 1 is a perspective view illustrating an absorbent article package according to a first embodiment of the present invention.

First, the absorbent article package 1 according to the first embodiment will be described with reference to FIGS. 1 to 9. The absorbent article package 1 according to the first embodiment includes a plurality of pet absorbent articles 10 and a packing bag 20 which stores the plurality of pet absorbent articles 10 as illustrated in FIG. 1.

Figure 2:
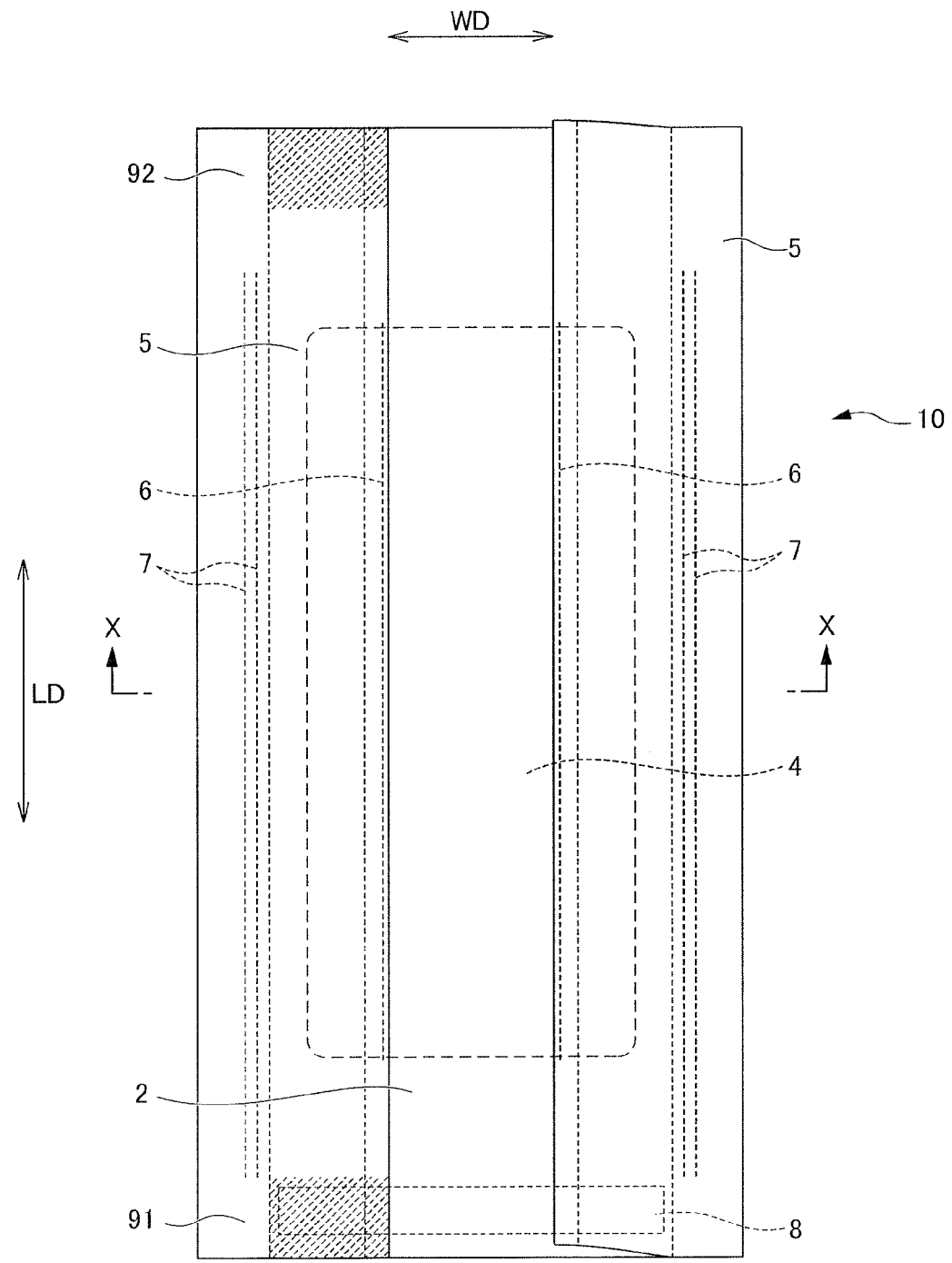
FIG. 2 is a plan view illustrating absorbent articles stored in the absorbent article package according to the first embodiment.
Figure 3:
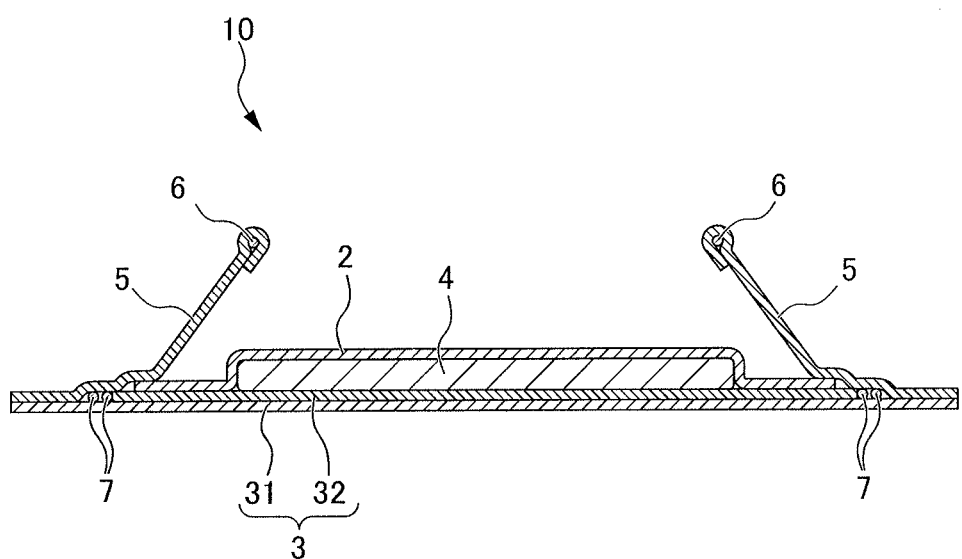
FIG. 3 is a cross-sectional view taken along the line X-X of FIG. 2.

First, a configuration of the pet absorbent article 10 according to the first embodiment will be described with reference to FIGS. 2 to 4. The pet absorbent article 10 is formed in a rectangular shape as illustrated in the plan view of FIG. 2. As illustrated in FIGS. 2 and 3, the pet absorbent article 10 includes a top sheet 2 as a liquid permeable surface layer, a liquid impermeable back surface layer (i.e., back sheet) 3, an absorbent core 4, a pair of side sheets 5 and 5, a first elastic member 6, a second elastic member 7, and a hook tape 8 as an engagement member.

The top sheet 2 is mainly a face for making direct contact with a body of the pet as a wearing target. This top sheet 2 is configured to include nonwoven fabric having pores or no pore that can be engaged with the hook tape 8 described below. In this embodiment, as a top sheet 2, air-through nonwoven fabric is used. The density of the nonwoven fabric that forms the top sheet 2 is 0.01 g/cm$^3$ to 1.0 g/cm$^3$.

The back sheet 3 includes a back surface sheet 31 which configures the body of the pet absorbent article 10 and a waterproof sheet 32 arranged on the top sheet side of the back surface sheet 31 as illustrated in FIG. 3.

The back surface sheet 31 is configured to include nonwoven fabric that can be engaged with the hook tape 8. More specifically, the back surface sheet 31 may be used of hydrophobic nonwoven fabric, a sheet obtained by laminating nonwoven fabric and an impermeable plastic film, spun bond nonwoven fabric, SMS non-woven fabrics obtained by inserting high water-resistant melt-blown nonwoven fabric between high strength spunbond nonwoven fabric, and the like. In this embodiment, as a back surface sheet 31, spun bond nonwoven fabric is used.

The waterproof sheet 32 may include an impermeable plastic film other than the material of the back surface sheet 31.

According to the first embodiment, the back surface sheet 31 is configured to include nonwoven fabric having a lower engaging force to the hook tape 8 than that of the nonwoven fabric of the top sheet 2. The density of the nonwoven fabric that forms the back surface sheet 31 is 0.001 g/cm$^3$ to 0.3 g/cm$^3$. As described above, the density of the top sheet 2 is 0.01 g/cm$^3$ to 1.0 g/cm$^3$ and the density of the back surface sheet 31 is 0.001 g/cm$^3$ to 0.3 g/cm$^3$. Thus, the density of the back surface sheet 31 is configured to be smaller than that of the top sheet 2.

Here, the engagement force is obtained by the following method.

First, the hook tape is cut into a test piece of 25 mm by 60 mm. An end portion of the test piece is held by a chuck by 10 mm. The nonwoven fabric such as the back surface sheet 31 or the top sheet 2, which is an engagement target of the hook tape, is stuck to a stainless panel with a double-stick tape. The test piece is placed on the engagement target and engaged therewith by a pressurizing roller of 700 g moving back and forth thereon at 300 mm/min. The stainless panel is set to a measuring instrument "Autograph" manufactured by Shimadzu Corporation. An end portion of the test piece is peeled from the stainless panel such that the test piece makes 135 degrees with respect to the stainless panel. Here, a value upon disengagement is measured as the engagement force (N) and engagement strength is obtained by dividing N by a width of the test piece (25 mm in the present measurement) (N/25 mm). Peeling of the test piece is performed under conditions of: a distance in a perpendicular direction between the chuck and the test piece (hook tape) of 10 mm; a pulling rate of 300 mm/min; an ambient temperature of 20 degrees centigrade; and relative humidity of 65%. The engagement force in the present embodiment is a value obtained by multiplying the engagement strength of the test piece thus obtained by a width of the back surface sheet 31 or the top sheet 2 according to the embodiment.

The absorbent core 4 is interposed between the top sheet 2 and the back surface layer 3 that are overlapped with each other as illustrated in FIG. 3. The absorbent core 4 which is made of fluff-like pulp or formed by coating a core wrap material, such as tissue, on high absorbent polymer may be used.

A pair of the side sheets 5 and 5 is formed in an elongated rectangular shape, and each side sheet 5 is arranged on the body side of the lateral portion along the longitudinal direction of the top sheet 2.

The outer edges of the pair of side sheets 5 and 5 are bonded to the lateral portion of the back surface sheet 31. A part of the inner edges of the pair of the side sheets 5 and 5 is free-ended. A water-repellent or hydrophobic material is preferably used in a pair of side sheets 5 and 5. Specifically, examples of the side sheet 5 may include various kinds of nonwoven fabric, such as spunlace nonwoven fabric, spunbond nonwoven fabric, thermal bonding nonwoven fabric, melt-blown nonwoven fabric, SMS nonwoven fabric, needle punching nonwoven fabric, and air-through nonwoven fabric. In this embodiment, as the side sheet 5, SMS nonwoven fabric is used. The density of nonwoven fabric that forms the side sheet 5 is 0.001 g/cm$^3$ to 0.3 g/cm$^3$. Here, the density of each of the top sheet 2, the back surface sheet 31, the side sheet 5 are obtained as following. First, each nonwoven fabric is cut into a 10×10 cm sample. The weight and thickness of the sample under no load is measured at an ambient temperature of 20 degrees centigrade and relative humidity of 65%. The values of the weight and the thickness are obtained respectively by averaging values obtained from the measurement of weight and thickness of ten samples.

The first elastic member 6 is arranged in the vicinity of each inner edge of a pair of side sheets 5 and 5. The second elastic member 7 is arranged in each of a pair of the lateral portions along the longitudinal direction LD of the pet absorbent article 10.

The first elastic member 6 and second elastic member 7 which are made of natural rubber, such as filamentous rubber of flat rubber, urethane, ethylene vinyl acetate copolymer (EVA), or thermoplastic elastomer, such as PE, may be used.

The hook tape 8 is arranged and bonded on the outer face of the back surface sheet 31 in the vicinity of a first end 91 of the pet absorbent article 10 in the longitudinal direction LD. The hook tape 8 has a band shape and is arranged such that the longitudinal direction of the hook tape 8 extends along the width direction WD of the pet absorbent article 10.

Figure 5:
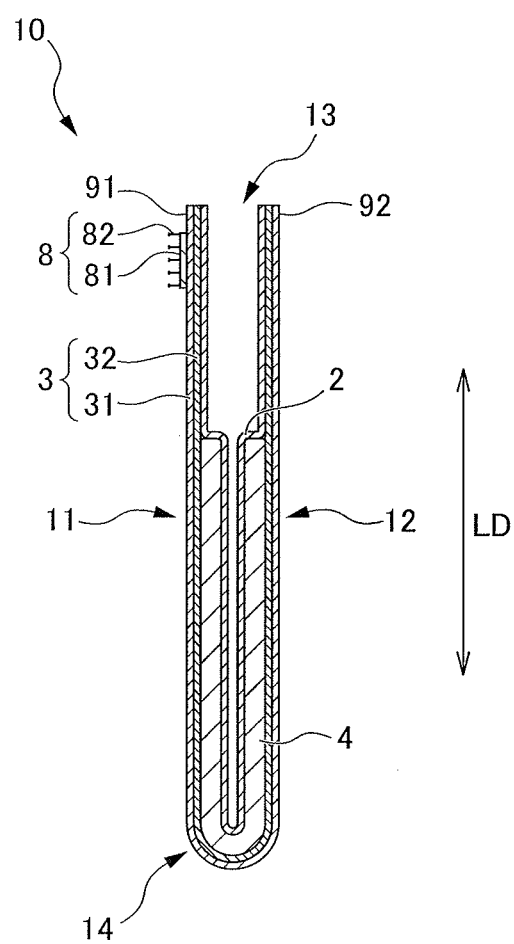
FIG. 5 is a vertical cross-sectional view illustrating a state that the absorbent article of FIG. 2 is folded.

The hook tape 8 includes a band-shaped base portion 81 and a plurality of hook portions 82 provided on one face of the base portion 81 (refer to FIG. 5). The hook tape 8 is configured to be engaged with the top sheet 2 by engaging a plurality of hook portions 82 with fibers of the nonwoven fabric of the top sheet 2. In addition, the hook tape 8 is configured to be engaged with the back surface sheet 31 by engaging a plurality of hook portions 82 with fibers of the nonwoven fabric of the back surface sheet 31.

The hook tape 8 is formed by integrating the base portion 81 and a plurality of hook portions 82 using synthetic resin material, such as polypropylene.

Figure 4:
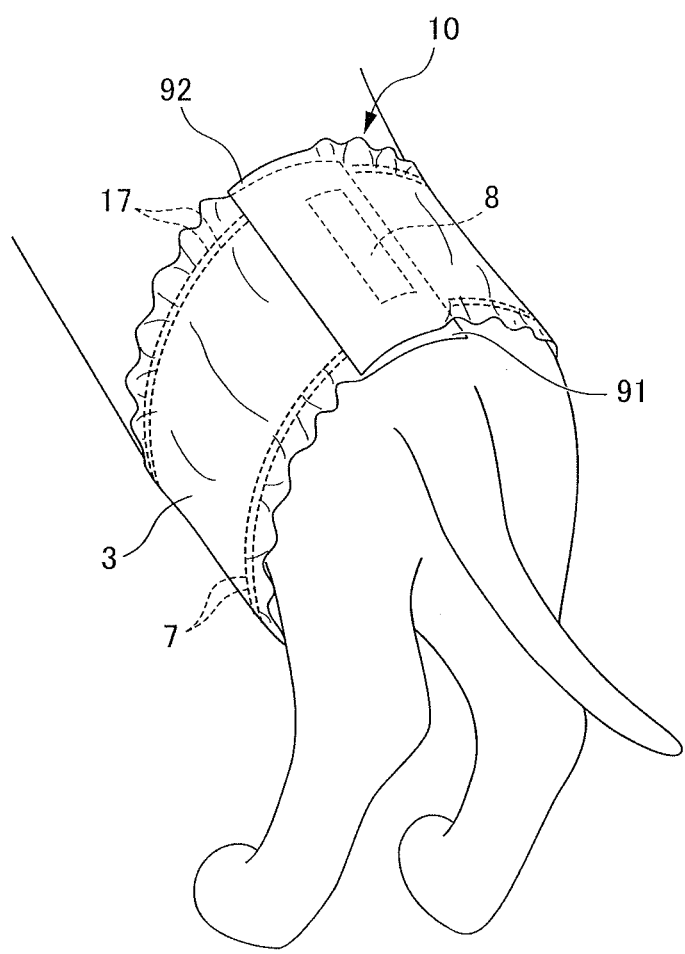
FIG. 4 is a diagram illustrating a state that the absorbent article of FIG. 2 is worn on a pet as a wearing target.

The pet absorbent article 10 described above is to be worn on the girth of the pet in use as illustrated in FIG. 4. Specifically, first, the first end 91 in the longitudinal direction LD of the pet absorbent article 10 is located on the back of the pet, and a second end 92 in the longitudinal direction LD is wound around to cover the ventral side of the pet while the vicinity of the first end 91 is pressed. Subsequently, the inner face of the second end 92 mainly configured of the top sheet 2 is engaged with the hook tape 8 arranged on the back surface sheet side of the first end 91. As a result, a state that the pet absorbent article 10 is wound around the body of the pet is maintained.

FIG. 5 is a vertical cross-sectional view illustrating a state that the pet absorbent article 10 is folded.

A plurality of pet absorbent articles 10 are each folded to define a first outer face 11 and a second outer face 12 as illustrated in FIG. 5.

According to the first embodiment, the pet absorbent article 10 is folded in half along the longitudinal direction LD such that the top sheet 2 faces inwardly (i.e., the top sheet 2 faces itself) as illustrated in FIG. 5. As a result, the folded pet absorbent article 10 includes a first end portion 13 having the first end 91 and the second end 92 in the folded longitudinal direction LD and a second end portion 14 arranged opposite to the first end portion 13 in the half-folded curved portion, so that a rectangular shape is formed such that a direction connecting the first and second end portions 13 and 14 becomes the longitudinal direction. In addition, both the first outer face 11 and the second outer face 12 of the folded pet absorbent article 10 are defined by the back surface sheet 31. The hook tape 8 is arranged in the vicinity of the first end portion 13 of the first outer face 11 of the folded pet absorbent article 10.

Figure 6:
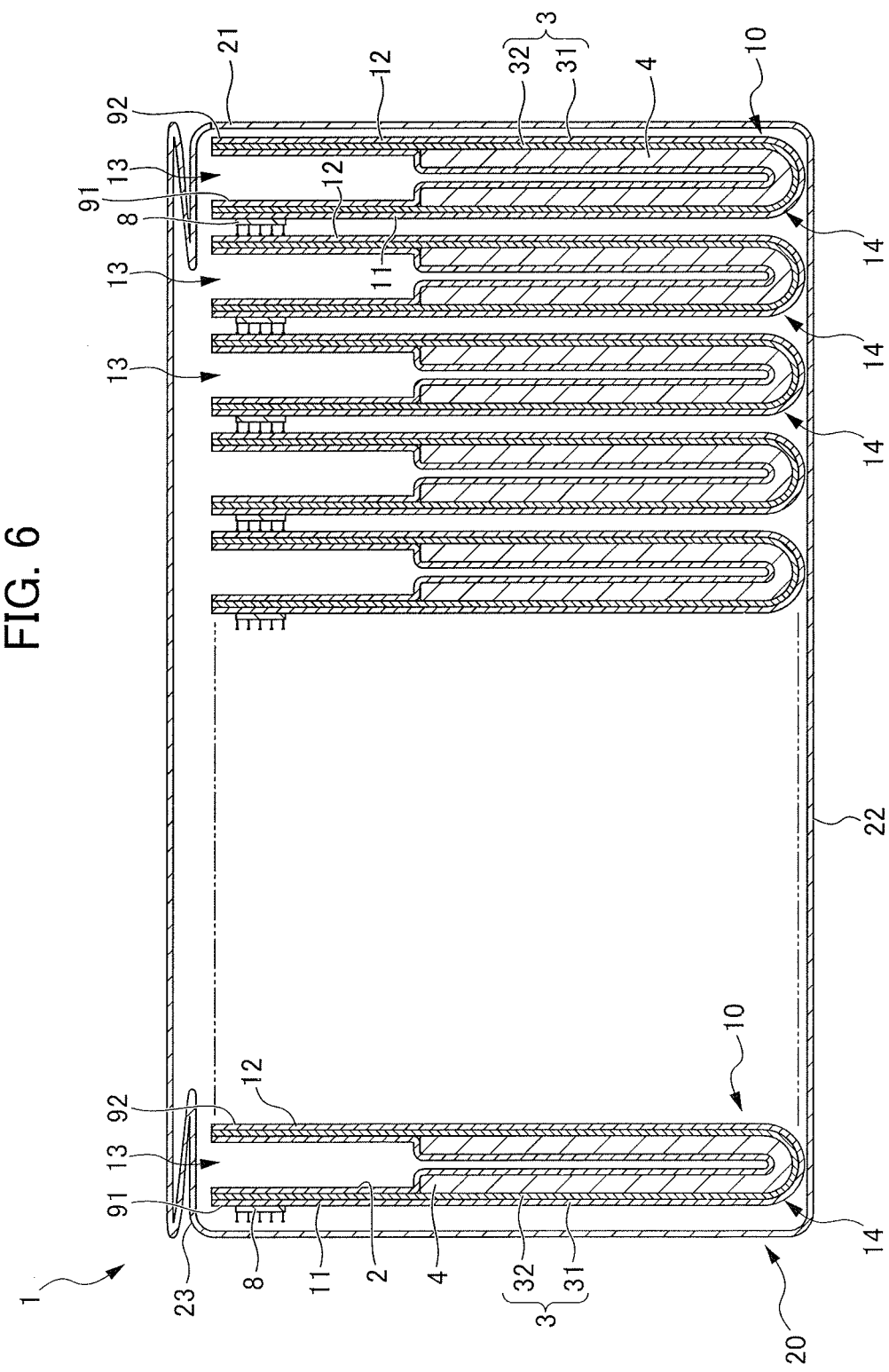
FIG. 6 is a cross-sectional view taken along the line Y-Y of FIG. 1.

A plurality of folded pet absorbent articles 10 are overlapped (arranged in a layered state) such that the first outer face 11 of one pet absorbent article 10 makes contact with the second outer face 12 of another pet absorbent article 10 adjacent to the one pet absorbent article 10 as illustrated in FIGS. 1 and 6. In addition, a plurality of pet absorbent articles 10 are overlapped such that the first end portions 13 are located on the same side, and the second end portions 14 are located on the same side.

Figure 8:
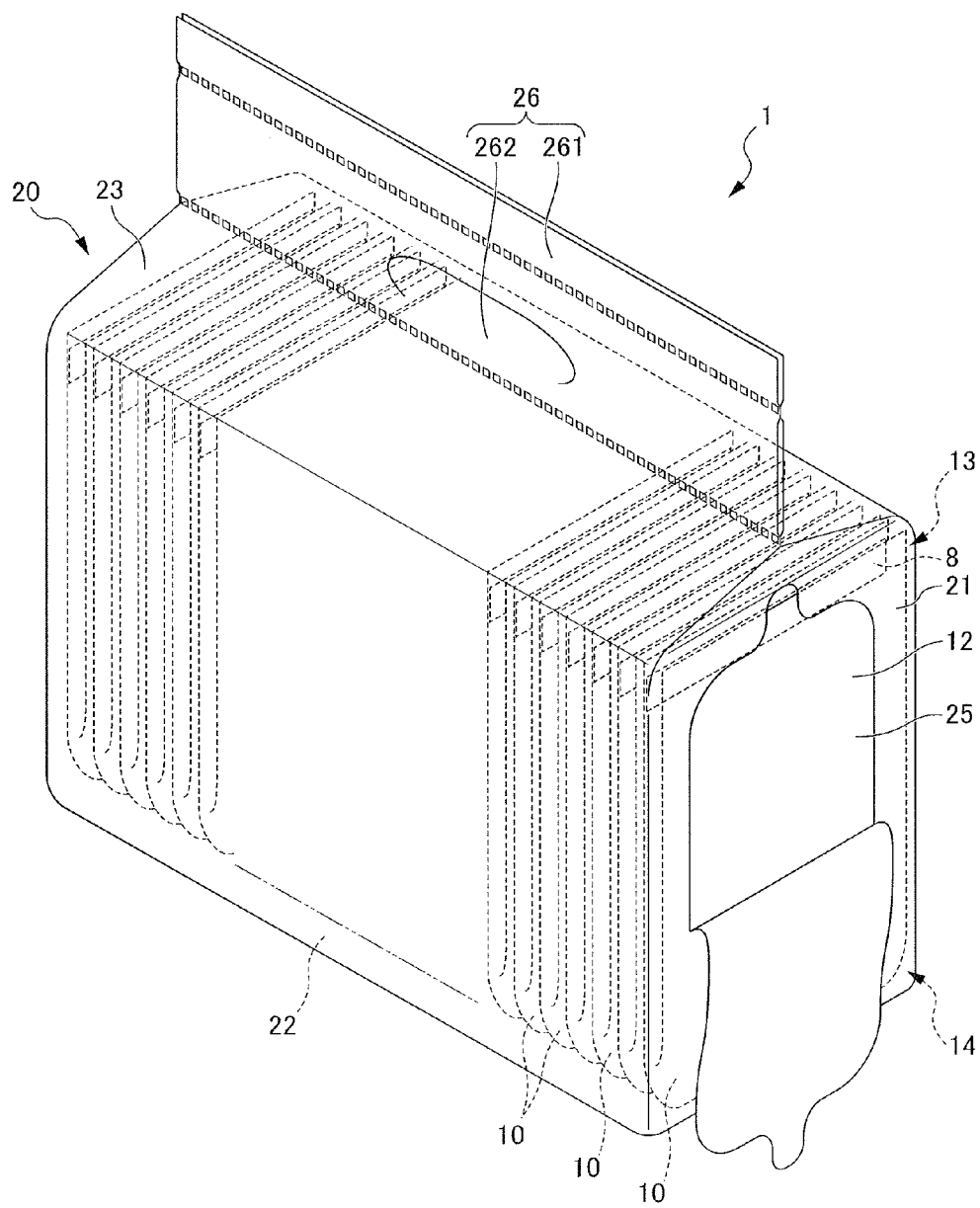
FIG. 8 is a perspective view illustrating a state that an opening is formed by tearing a tearable portion of the packing bag in the absorbent article package of FIG. 1.

The packing bag 20 is formed in a bag shape using a flexible sheet member to store a plurality of folded and overlapped pet absorbent articles 10. A plurality of pet absorbent articles 10 are stored in the packing bag 20 in a compressed state. As illustrated in FIGS. 1 and 8, the packing bag 20 includes four side faces including the first face 21, a bottom face 22, a top face 23, a tearable portion 24 for forming an opening 25 in the first face 21, and a grip portion 26 provided in the top face 23.

The first face 21 is arranged to face the second outer faces 12 of a plurality of pet absorbent articles 10 stored in the packing bag 20 as illustrated in FIG. 6. In other words, the first face 21 is located on an extension line in the stacking direction of a plurality of pet absorbent articles 12. According to the first embodiment, the first face 21 is formed to have nearly the same shape and size as those of the first or second outer faces 11 and 12 of the folded pet absorbent article 10. That is, the area of the first face 21 is nearly equal to the area of the first outer face 11 and the area of the second outer face 12 of the folded pet absorbent article 10.

The bottom face 22 is arranged on the side where the second end portions 14 of a plurality of pet absorbent articles 10 stored in the packing bag 20 are located.

The top face 23 is arranged on the side where the first end portions 13 of a plurality of pet absorbent articles 10 stored in the packing bag 20 are located.

According to the first embodiment, the bottom face 22 and the top face 23 are formed in a rectangular shape such that the stacking direction of a plurality of pet absorbent articles 10 becomes the longitudinal direction as illustrated in FIGS. 1 and 8.

Figure 7:
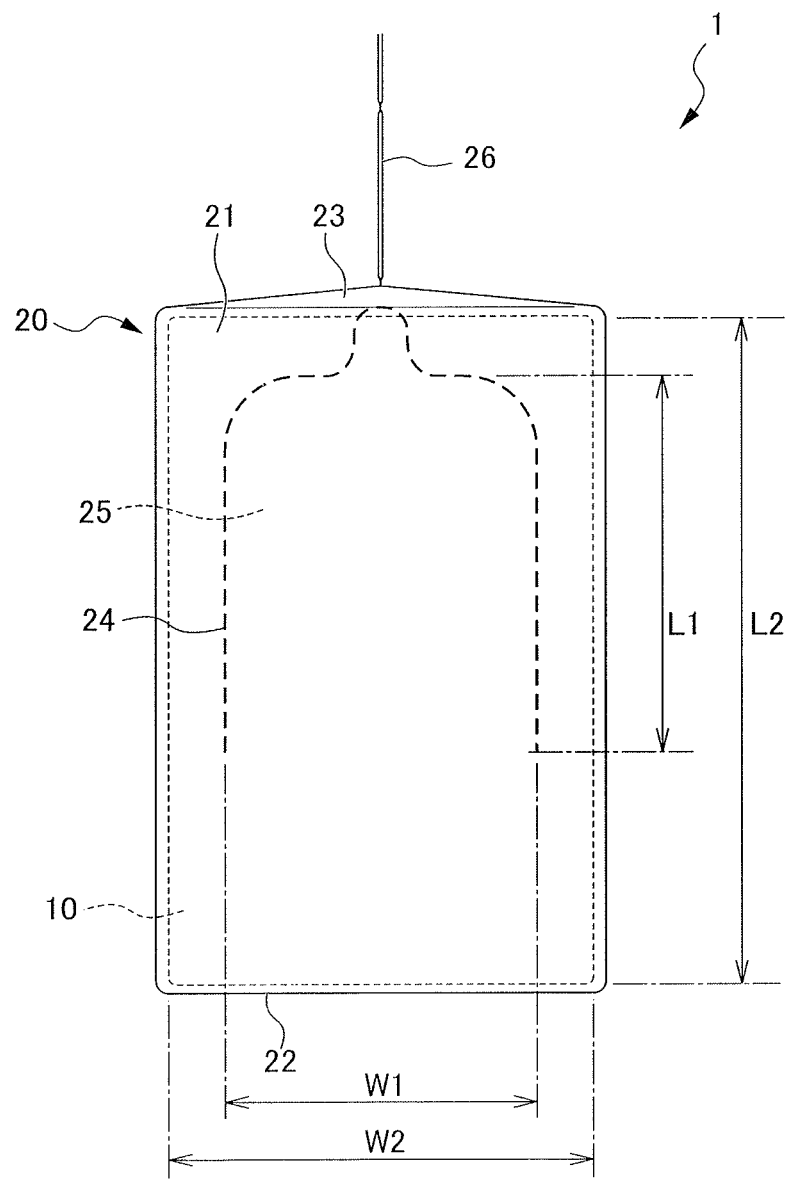
FIG. 7 is a front view illustrating a first face of the packing bag.

The tearable portion 24 is formed by a perforated line formed in a sheet member of the first face 21 as illustrated in FIG. 7. The tearable portion 24 extends along the side edge of the first face 21 adjacent the top face 23, and also extends toward the bottom face 22 along the side edge of the first face 21 that connects the top face 23 and the bottom face 22. In addition, a center of the top part of the tearable portion 24 on the top face side is curved to be convex.

The end portions of the tearable portion 24 are spaced from the bottom face 22 toward the top face 23 by a predetermined distance. That is, the tearable portion 24 is formed on the top face side (the side where the first end portion 13 of the folded pet absorbent article 10 is located) of the first face 21. The area where the tearable portion 24 is not formed is provided on the bottom face side on the first face 21 (the side where the second end portion 14 of the folded pet absorbent article 10 is located).

The opening 25 is formed by tearing the tearable portion 24 as illustrated in FIG. 8. That is, the opening 25 is formed in a position placed toward the top face side of the first face 21 where the first end portion 13 of the folded pet absorbent article 10 is positioned. The opening 25 is not formed on a side where the second end portion is positioned.

The length L1 (in the direction connecting the top face 23 and the bottom face 22) of the opening 25 is preferably 20% to 80%, and more preferably, 40% to 70%, of the longitudinal length L2 (in the direction connecting the top face 23 and the bottom face 22) of the first face 21 for easy extraction of the pet absorbent articles 1 stored in the packing bag 20 one by one.

The width W1 (perpendicular to the length L1) of the opening 25 is preferably 50% to 90%, and more preferably, 65% to 80%, of the width W2 (perpendicular to the direction connecting the first and second end portions 13 and 14) of the folded pet absorbent article 10.

In addition, the area of the opening 25 is preferably 30% to 70% of the area of the first outer face 11 of the pet absorbent article 10.

The grip portion 26 includes an extension 261 and a handle portion 262 formed in the extension 261 as illustrated in FIGS. 1 and 8. The extension 261 is formed by extending the sheet member from the top face 23. The extension 261 is arranged in the center of the top face 23 in the width direction and extends in the longitudinal direction of the top face 23.

The handle portion 262 is provided in the approximate center of the extension 261 and is formed by cutting out a part of the sheet member of the extension 261.

In the package 1 described above, a plurality of pet absorbent articles 10 are stored in the packing bag 20 in a compressed state as illustrated in FIG. 6. For this reason, each first outer face 11 of a plurality of pet absorbent articles 10 stored in the packing bag 20 abuts on the second outer face 12 of the adjacent pet absorbent article 10. Here, the first outer face 11 of each first end portion 13 of a plurality of folded pet absorbent articles 10 is provided with a hook tape 8 to be engaged with the top sheet 2 when wearing the pet absorbent article 10 on the pet. In addition, the second outer face 12 of the folded pet absorbent article 10 is configured to include nonwoven fabric (back surface sheet 31) that can be engaged with the hook tape 8. As a result, the hook tapes 8 provided in a plurality of pet absorbent articles 10 are engaged with the second outer faces 12 of the adjacent pet absorbent articles 10.

Next, a sequence of extracting the pet absorbent articles 10 stored in the packing bag 20 of the absorbent article package 1 according to the first embodiment will be described with reference to FIGS. 1, 8, and 9A to 9D.

The absorbent article package 1 according to the first embodiment is carried by holding the grip portion 26 and is placed on a predetermined storage site such that the bottom face 22 faces the ground (refer to FIG. 1). In this state, the first face 21 is a standing surface, and the first and second outer faces 11 and 12 of each of a plurality of pet absorbent articles 10 are also arranged in a standing state. In addition, the tearable portion 24 (opening 25) is formed in a position placed toward the upper side of the first face 21.

Figure 9A:
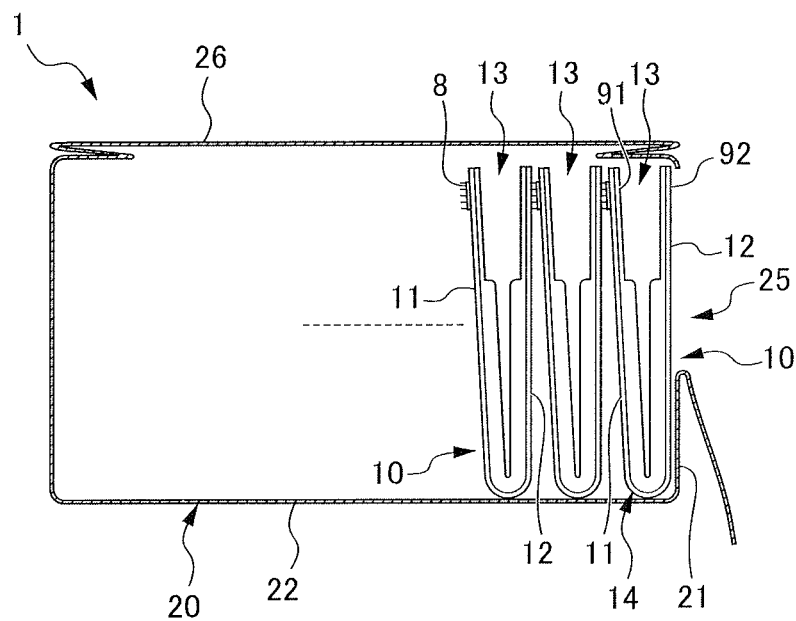
FIG. 9A is a diagram illustrating a sequence of extracting the absorbent articles stored in the packing bag of the absorbent article package according to the first embodiment, in which the opening is formed by tearing the tearable portion.

When the first pet absorbent article 10 stored in the packing bag 20 is initially extracted in this state, first, the opening 25 is formed by tearing the tearable portion 24 as shown in FIG. 8. Then, as shown in FIGS. 8 and 9A, the second outer face 12 of the first pet absorbent article 10 arranged nearest to the opening 25 among a plurality of pet absorbent articles 10 stored in the packing bag 20 is exposed from the opening 25.

Figure 9B:
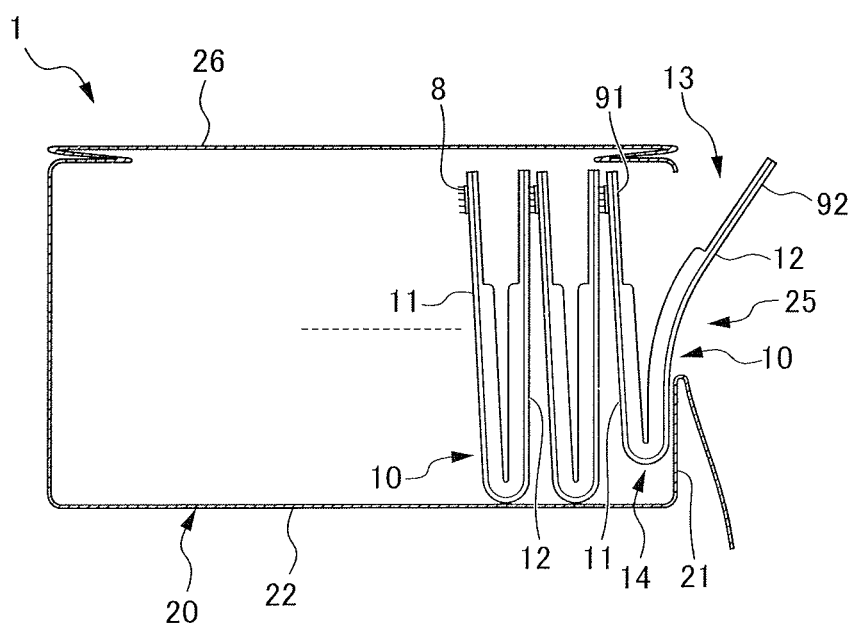
FIG. 9B is a diagram illustrating a state that a first end portion of a second outer face of the first absorbent article arranged nearest to the opening is extracted in the state of FIG. 9A.

Subsequently, as shown in FIG. 9B, the first end portion 13 of the first pet absorbent article 10 is picked and the first pet absorbent article 10 is extracted from the opening 25. Here, according to the first embodiment, the opening 25 is located on the first face 21 in a position placed toward the side where the first end portion 13 of the pet absorbent article 10 is located. In addition, the first end portion 13 includes the first end 91 (on the first outer face side) and the second end 92 (on the second outer face side) in the longitudinal direction LD of the folded and overlapped pet absorbent articles 10. As a result, out of the first end portion 13 including the first end 91 and second end 92, only the second end 92 (on the second outer face side) exposed through the opening 25 can be easily extracted.

Figure 9C:
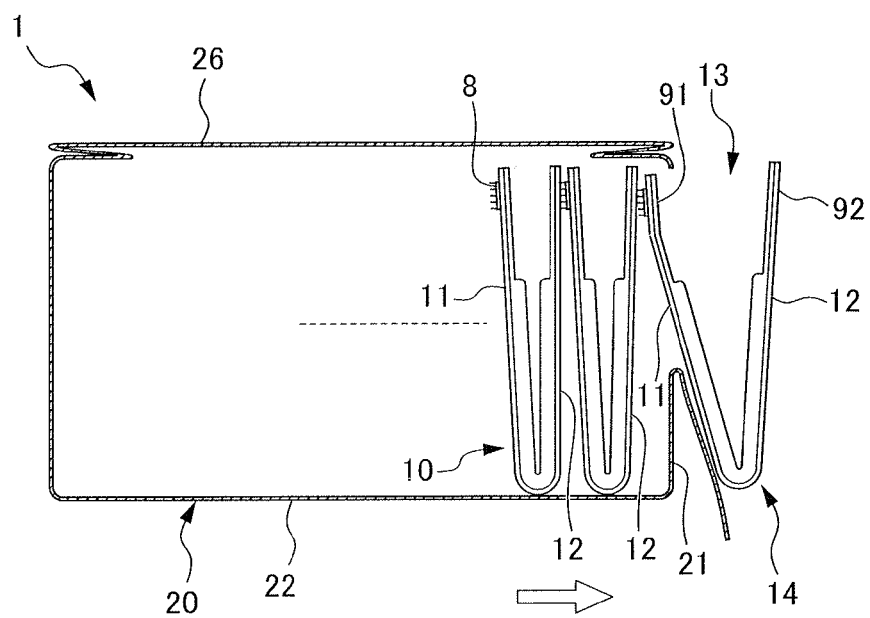
FIG. 9C is a diagram illustrating a state that the first end portion is further extracted in the state of FIG. 9B so that a second end portion is extracted from the opening.

While the second end 92 of the first pet absorbent article 10 is pulled out as shown in FIG. 9B, the second end portion 14 is extracted and escaped to the outside of the opening 25 as shown in FIG. 9C.

Figure 9D:
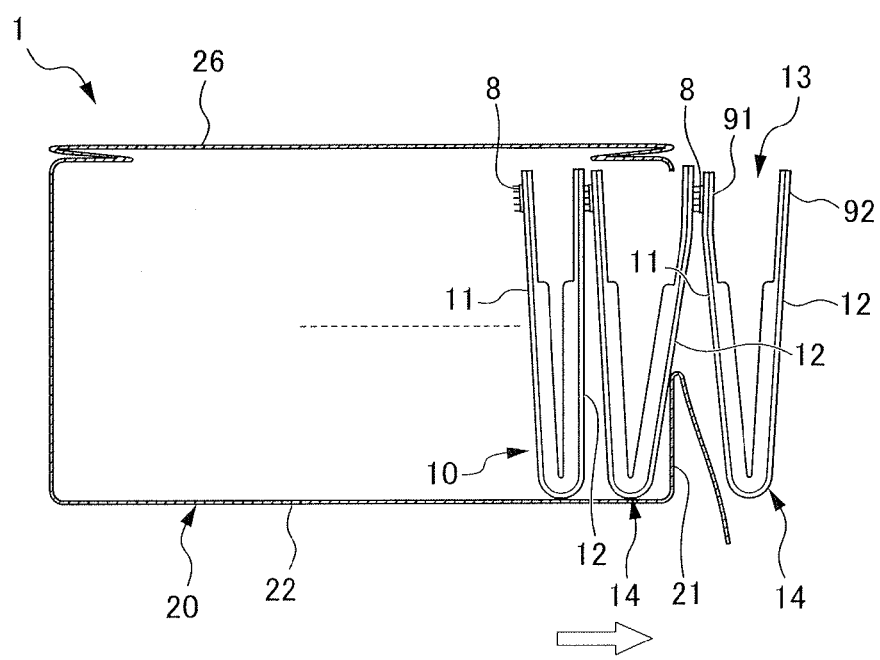
FIG. 9D is a diagram illustrating a state that the first absorbent article is further extracted in the state of FIG. 9C.

When the first pet absorbent article 10 is further extracted, the first end 91 (on the first outer face side) of the first end portion 13 is escaped to the outside of the opening 25 as shown in FIG. 9D. Here, the hook tape 8 is arranged on the first outer face 11 of the first end portion 13 and is engaged with the second outer face 12 of the second pet absorbent article 10. As a result, as the first outer face side of the first pet absorbent article 10 is extracted to the outside of the opening 25, the second pet absorbent article 10 is pulled out and moved toward the opening 25.

Figure 9E:
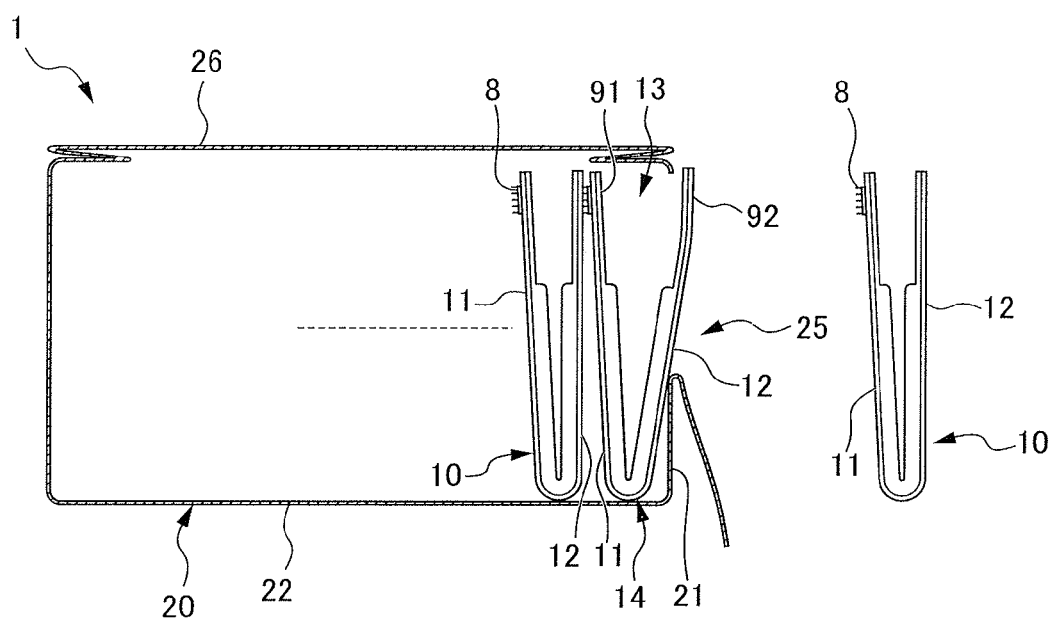
FIG. 9E is a diagram illustrating a state that the first absorbent article is extracted, and the second absorbent article is located in the vicinity of the opening.

In this state, when the first pet absorbent article 10 is further extracted, a portion where the opening 25 is not formed in the lower portion of the first face 21 interferes with the second end portion 14 of the second pet absorbent article 10 so as to apply a force of suppressing the movement of the second pet absorbent article 10 toward the opening 25. As a result, while an extracting force is applied to the first pet absorbent article 10, a force of suppressing the movement is applied to the second pet absorbent article 10. Therefore, the engagement between the hook tape 8 of the first pet absorbent article 10 and the second outer face 12 of the second pet absorbent article 10 is released. Accordingly, as shown in FIG. 9E, the first pet absorbent article 10 is separated from the second pet absorbent article 10. In addition, the second pet absorbent article 10 is moved to the vicinity of the opening 25, and the second outer face 12 of the second pet absorbent article 10 is exposed from the opening 25.

The same sequence is repeated when the second and subsequent pet absorbent articles 10 are extracted. As a result, by virtue of the operation of extracting the pet absorbent article 10 from the opening 25, it is possible to move the adjacent pet absorbent article 10 to the vicinity of the opening 25. Therefore, even when the number of pet absorbent articles 10 stored in the packing bag 20 is reduced, it is possible to easily extract the pet absorbent articles 10 one by one.

Next, the manufacturing method of the absorbent article package 1 according to the first embodiment is described.

In the packing bag 20 of the first embodiment, the perforated line that forms the tearable portion 24 is formed by a cutter in a predetermined portion of the sheet member forming the packing bag 20. The sheet member in which the perforated line is formed has a tube shape and is conveyed such that its longitudinal direction is in the direction of conveying. The tube shaped sheet member is heat-sealed in a lateral direction, at predetermined intervals in the direction of conveying. Consequently, portions in the vicinity of the heat sealed portion at the rear side with respect to the direction of conveying, is cut in a lateral direction.

The heat sealed portion forms the bottom face 22 of the packing bag. An end opposing the bottom face forms an opening part by a cutting, and the pet absorbent articles 10 are stored in a layered state from the opening part. At this time, the pet absorbent articles 10 are stored so that a second outer face 12 of the pet absorbent articles makes contact at a position at which the tearable portion 24 is formed.

When the pet absorbent articles are stored in the tube shaped sheet member, the opening part is sealed by heat-sealing. At this occasion, the tube shaped sheet member is heat-sealed in 2 places so as to extend in a lateral direction at intervals in the direction of conveying. An incision is formed between the 2 heat-sealed places to form a handle portion 262.

In the absorbent article package 1 according to the first embodiment described above, it is possible to obtain the following advantages and effects.

(1) The pet absorbent article 10 is folded to provide the first and second outer faces 11 and 12, the hook tape 8 is arranged on the first outer face 11, and the second outer face 12 includes the back surface sheet 31 that can be engaged with the hook tape 8. In addition, a plurality of folded pet absorbent articles 10 are stored in the packing bag 20 in an overlapped state while the first outer face 11 of one pet absorbent article 10 makes contact with the second outer face 12 of the pet absorbent article 10 adjacent to the one pet absorbent article 10, and the opening 25 is formed on the first face 21 facing the second outer faces 12 of the pet absorbent articles 10 in this packing bag 20. As a result, the hook tapes 8 arranged in a plurality of pet absorbent articles 10 are engaged with the second outer faces 12 of the adjacent pet absorbent articles 10. Therefore, it is possible to move the pet absorbent article 10 adjacent to the extracted pet absorbent article 10 toward the opening 25 as the pet absorbent article 10 is extracted to the outside of the opening 25. Therefore, by virtue of the operation of extracting one pet absorbent article 10 from the opening 25, it is possible to move the adjacent pet absorbent article 10 to the vicinity of the opening 25. As a result, it is possible to easily extract the pet absorbent articles 10 one by one even when the number of pet absorbent articles 10 stored in the packing bag 20 is reduced.

(2) The packing bag 20 includes the tearable portion 24, and the opening 25 is formed by tearing the tearable portion 24. As a result, it is possible to easily form the opening 25.

(3) The folded pet absorbent article 10 has a rectangular shape including the first and second end portions 13 and 14, the hook tape 8 is arranged in the vicinity of the first end portion 13 on the first outer face 11, and the opening 25 is to be formed on the first face 21 on the side where the first end portion 13 is located. As a result, when the first pet absorbent article 10 is extracted, it is possible to pick and extract only the second outer face 12 of the first end portion 13. In addition, since the opening 25 is not provided in the first face 21 on the side where the second end portion 14 is located, the portion of the first face 21 where the opening 25 is not formed interferes with the second end portion 14 of the second pet absorbent article 10 adjacent to the first absorbent article 10 when the first pet absorbent article 10 is extracted, so that a force of suppressing the movement of the second pet absorbent article 10 toward the opening 25 is applied. Therefore, while an extracting force is applied to the first pet absorbent article 10, a force of suppressing the movement is applied to the second pet absorbent article 10. Accordingly, it is possible to suitably separate the first and second pet absorbent articles 10.

(4) In each of a plurality of pet absorbent articles 10 stored in the packing bag 20, a plurality of first end portions 13 are arranged to face the top face 23 of the packing bag 20, and the packing bag 20 includes the grip portion 26 provided on the top face 23. As a result, when the absorbent article package 1 is carried by holding the grip portion 26, it is possible to easily place the absorbent article package 1 such that the bottom face 22 faces the ground. As a result, the first face 21 becomes a standing surface, and the first and second outer faces 11 and 12 of each of a plurality of pet absorbent articles 10 can be also arranged in a standing state. In addition, the tearable portion 24 (opening 25) can be arranged in the upper portion of the first face 21. Therefore, since the opening 25 can be arranged in the upper portion of the standing first face 21, it is possible to easily extract the pet absorbent article 10 from the packing bag 20.

(5) The pet absorbent article 10 is formed in a rectangular shape including the top sheet 2 that is engageable with the hook tape 8, the back sheet 3 that is engageable with the hook tape 8, and the absorbent core 4. The hook tape 8 is arranged on the back surface layer 3 in the vicinity of the first end 91 in the longitudinal direction LD of the pet absorbent article 10. In addition, the pet absorbent article 10 is folded in half along the longitudinal direction LD, and the back surface layer 3 defines the first and second outer faces 11 and 12. As a result, using the hook tape 8 which is arranged to fasten the pet absorbent article 10 on a pet, the adjacent pet absorbent articles 10 arranged in a folded state can be engaged with each other. Therefore, by extracting one pet absorbent article 10 from the opening 25, it is possible to move the adjacent pet absorbent article 10 to the vicinity of the opening 25 without having to separately form a member for engaging the adjacent pet absorbent articles 10 with each other.

(6) The engaging force between the nonwoven fabric of the back surface sheet 31 and the hook tape 8 is lower than the engaging force between the nonwoven fabric of the top sheet 2 and the hook tape 8. As a result, it is possible to set the engaging force between the adjacent pet absorbent articles 10 arranged in a folded state to be lower than the engaging force for engaging the hook tape 8 with the top sheet 2 when the pet absorbent article 10 is worn on a pet. Therefore, since the adjacent, folded pet absorbent articles 10 can be engaged with each other weakly, it is possible to suitably separate the adjacent pet absorbent articles when one pet absorbent article 10 is extracted from the opening 25.

Next, the absorbent article package according to the second embodiment will be described with reference to FIGS. 10A to 10E. In the description of the following embodiments, the same constituent features as those described with respect to the first embodiment are referred by the same reference numerals and a description thereof is omitted or simplified.

The absorbent article package 1 according to the second embodiment is different from that according to the first embodiment mainly in the position of the opening 25.

Figure 10A:
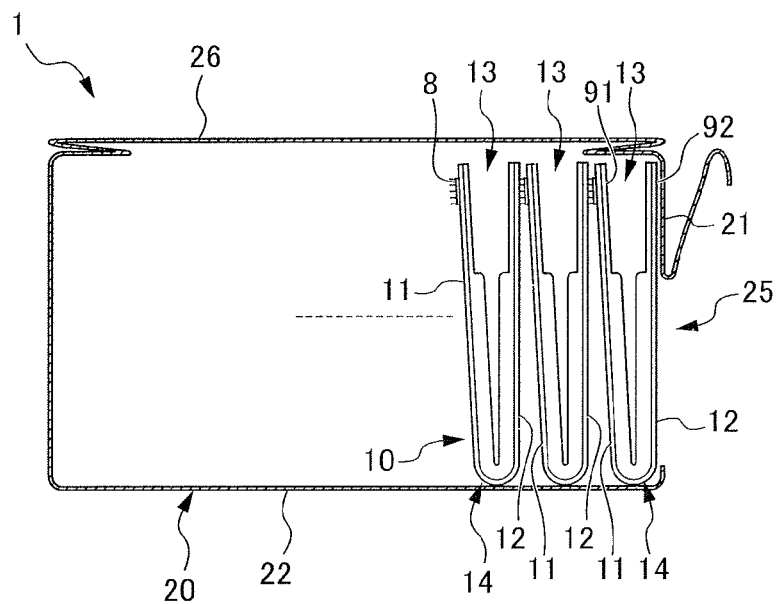
FIG. 10A is a diagram illustrating a sequence of extracting the absorbent articles stored in the packing bag of the absorbent article package according to a second embodiment, in which the opening is formed by tearing the tearable portion.

According to the second embodiment, as shown in FIG. 10A, the opening 25 is to be formed on the side where the second end portion 14 of the folded pet absorbent article 10 is positioned, that is, on the bottom face side of the first face 21. The opening is not formed on a side where the first end portion 13 is positioned.

According to the second embodiment, the tearable portion extends along the side edge of the first face 21 on the bottom face side, and also extends toward the top face 23 along the side edge of the first face 21 that connects the top face 23 and the bottom face 22. As a result, according to the second embodiment, the sheet member which covers the opening 25 is tucked up over the opening 25 while the opening 25 is formed as shown in FIG. 10A.

According to the second embodiment, the pet absorbent articles 10 stored in the packing bag 20 are extracted as follows.

In the absorbent article package 1 according to the second embodiment, the tearable portion 24 (opening 25) is arranged in a position placed toward the lower portion of the first face 21 while the packing bag 20 is placed such that the bottom face 22 faces the ground as shown in FIG. 10A.

In this state, when the opening 25 is formed by tearing the tearable portion 24, the second outer face 12 of the second end portion 14 of the first pet absorbent article 10 is exposed from the opening 25 as shown in FIG. 10A.

Figure 10B:
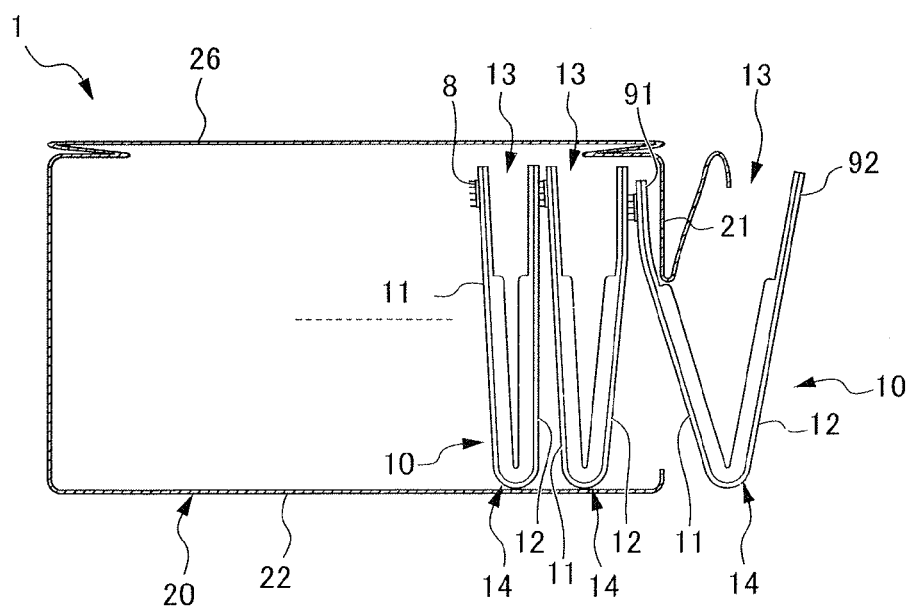
FIG. 10B is a diagram illustrating a state that the second end portion of the first absorbent article arranged nearest to the opening is extracted in the state of FIG. 10A.
Figure 10C:
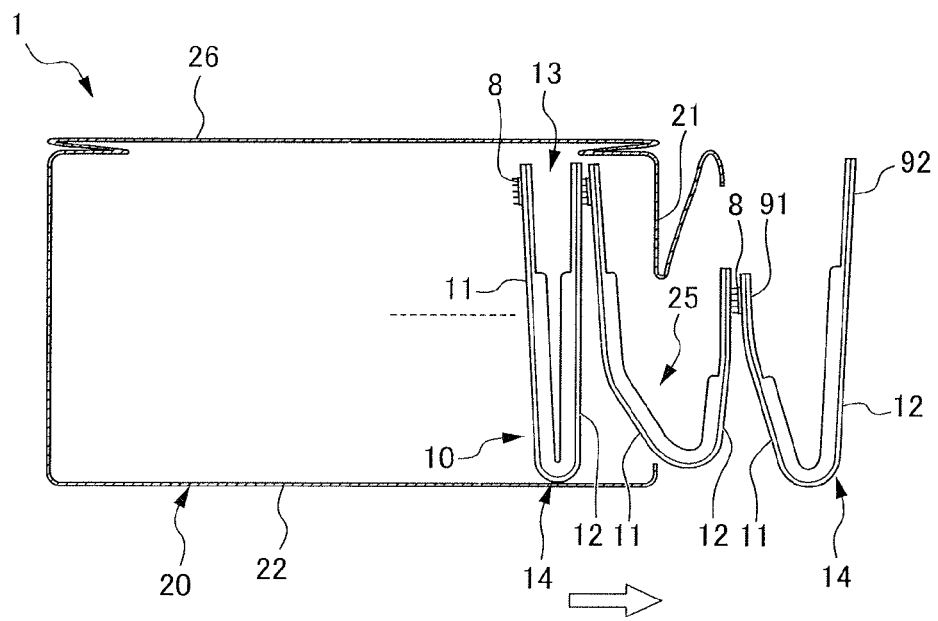
FIG. 10C is a diagram illustrating a state that the first absorbent article is further extracted in the state of FIG. 10B so that a second outer face side of the second absorbent article is extracted.

Then, as shown in FIG. 10B, the first pet absorbent article 10 is extracted from the opening 25 by picking the second end portion 14 of the pet absorbent article 10. Then, as shown in FIG. 10C, as the first end 91 of the first pet absorbent article 10 is extracted, the second end 92 of the second pet absorbent article 10 engaged with the first pet absorbent article 10 is escaped from the opening 25.

Figure 10D:
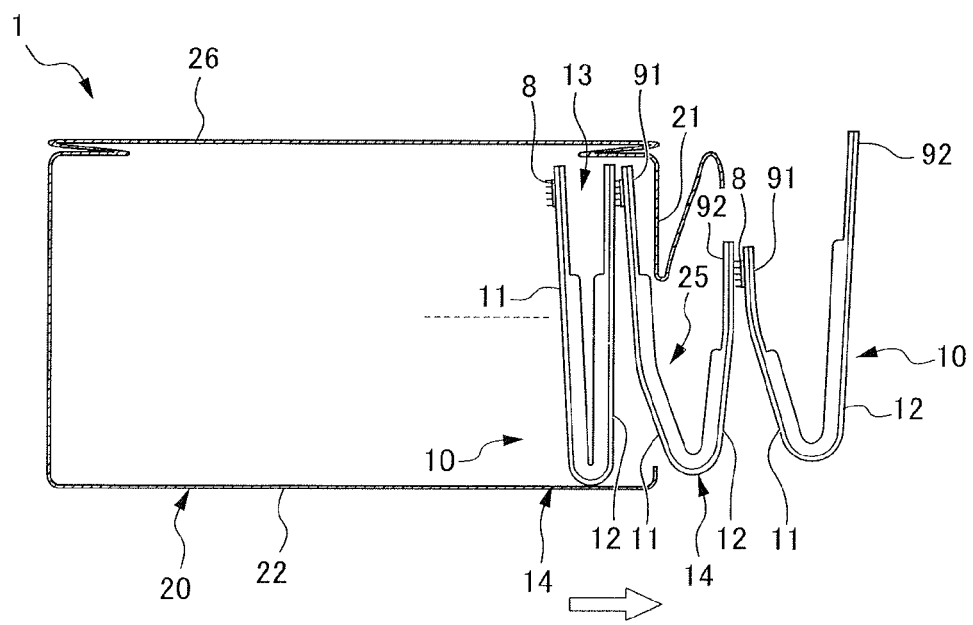
FIG. 10D is a diagram illustrating a state that the first absorbent article is further pulled out in the state of FIG. 10C.
Figure 10E:
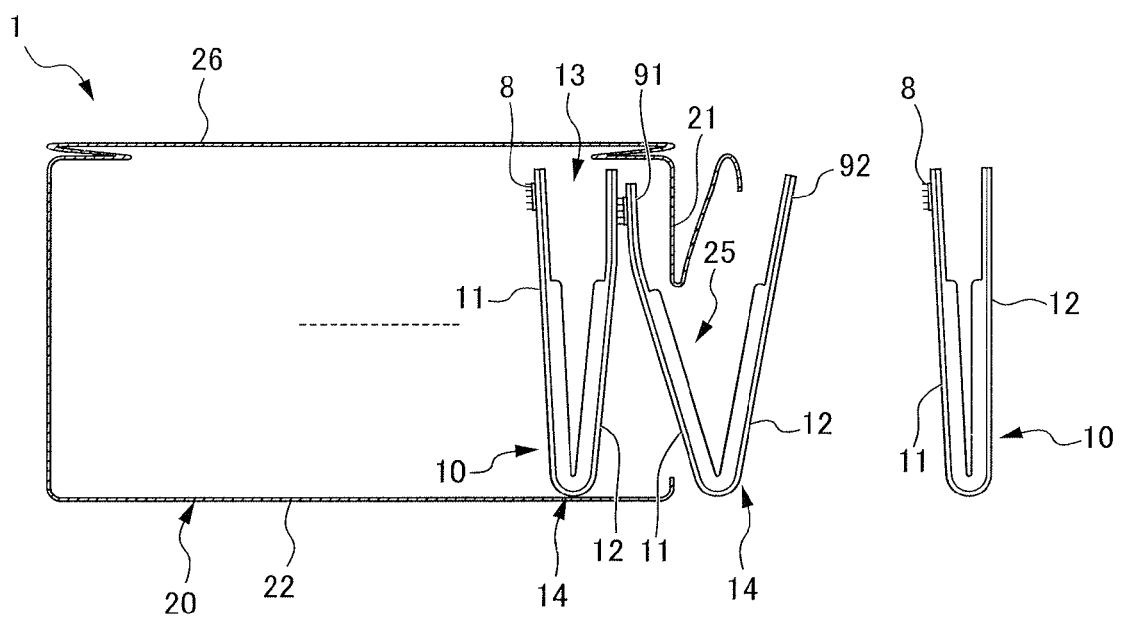
FIG. 10E is a diagram illustrating a state that the first absorbent article is extracted, and the second absorbent article is located in the vicinity of the opening.

In this state, as the first pet absorbent article 10 is further extracted, the first outer face 11 of the second end portion 14 of the second pet absorbent article 10 is pulled out from the opening 25 as shown in FIG. 10D. In addition, as the first pet absorbent article 10 is further extracted, the upper portion of the first face 21 where the opening 25 is not formed interferes with the first end 91 of the second pet absorbent article 10 so as to suppress the movement of the second pet absorbent article 10 toward the opening 25. As a result, while a pulling force is applied to the first pet absorbent article 10, a force of suppressing the movement is applied to the first end 91 of the second pet absorbent article 10. Therefore, the engagement between the hook tape 8 of the first pet absorbent article 10 escaped to the outside of the opening 25 and the second outer face 12 of the second pet absorbent article 10 is released. Then, the first pet absorbent article 10 is separated from the second pet absorbent article 10 as shown in FIG. 10E. In addition, the second pet absorbent article 10 is arranged in the vicinity of the opening 25 with the second outer face 12 escaped from the opening 25.

In the absorbent article package 1 according to the second embodiment, it is possible to obtain the following advantages and effects in addition to the advantages and effects (1), (2), (5), and (6) described above.

(7) The opening 25 is arranged on the side where the second end portion 14 of the folded pet absorbent article 10 is located. As a result, when the first pet absorbent article 10 is extracted, it is possible to arrange the second pet absorbent article 10 with the second outer face 12 escaped from the opening 25. Therefore, since the second and subsequent pet absorbent articles 10 stored in the packing bag 20 can be arranged with a part of the pet absorbent article 10 escaped from the opening 25, it is possible to easily extract the pet absorbent article 10 stored in the packing bag 20.

(8) The tearable portion extends along the side edge of the first face 21 on the bottom face side, and also extends toward the top face 23 along the side edge of the first face 21 that connects the top face 23 and the bottom face 22. As a result, the sheet member which covers the opening 25 can be positioned on the upper side of the opening 25 while the opening 25 is formed. Therefore, since the opening 25 can be covered by the torn sheet member after the package 1 is opened, it is possible to prevent external matter, such as garbage and the like, from entering the packing bag 20 after the package 1 is opened.

Figure 11:
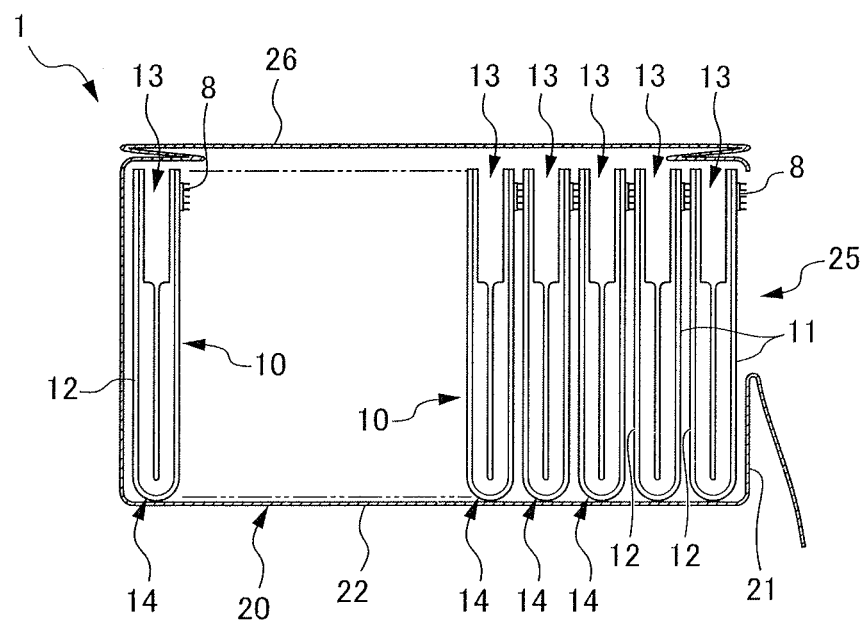
FIG. 11 is a cross-sectional view illustrating a state that a plurality of absorbent articles are stored in the packing bag of the absorbent article package according to a third embodiment.

Next, the absorbent article package 1 according to the third embodiment will be described with reference to FIG. 11. FIG. 11 is a diagram illustrating a state that a plurality of pet absorbent articles 10 are stored in the packing bag 20 of the absorbent article package according to the third embodiment.

The absorbent article package 1 according to the third embodiment is different from that according to the first embodiment in the direction in which a plurality of pet absorbent articles 10 are stored in the packing bag 20.

According to the third embodiment, a plurality of pet absorbent articles 10 are stored in the packing bag 20 such that the first outer face 11 where the hook tape 8 is arranged faces the first face 21 as shown in FIG. 11.

In the absorbent article package 1 according to the third embodiment, it is possible to obtain the advantages and effects (1) to (6) described above. In addition, the hook tape 8 exposed from the opening 25 exhibit a relatively higher friction coefficient than a remainder of the pet absorbent article 10, and facilitates gripping of the pet absorbent articles 10 to be extracted by the user's fingers.

Figure 12:
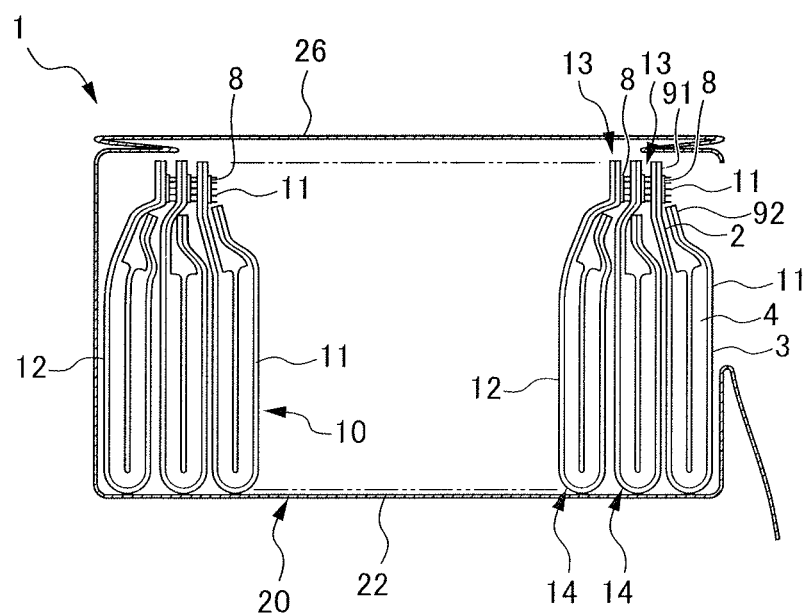
FIG. 12 is a diagram illustrating a state that a plurality of absorbent articles are stored in the packing bag of the absorbent article package according to a fourth embodiment.

Next, the absorbent article package 1 according to the fourth embodiment will be described with reference to FIG. 12. FIG. 12 is a diagram illustrating a state that a plurality of pet absorbent articles 10 are stored in the packing bag 20 of the absorbent article package according to the fourth embodiment.

The absorbent article package 1 according to the fourth embodiment is different from that according to the third embodiment in the arrangement of the hook tape 8 in the pet absorbent article 10 and in the folding of the pet absorbent article 10.

According to the fourth embodiment, the hook tape 8 is arranged on the top sheet side of the first end 91 in the longitudinal direction of the pet absorbent article 10 as shown in FIG. 12. In addition, the pet absorbent article 10 is folded asymmetrically in the longitudinal direction of the pet absorbent article 10 such that the top sheet 2 faces inwardly, and a portion of the first end 91 where the hook tape 8 is arranged to project upwardly beyond the second end 92. As a result, according to the fourth embodiment, the top sheet 2 and the hook tape 8 arranged on the top sheet 2 are included in the upwardly projecting first end 91 and on the first outer face 11 of the folded pet absorbent article 10, and the hook tape 8 is engaged with the back surface sheet 31 in the upwardly projecting first end 91 of the adjacent pet absorbent article 10.

In the absorbent article package 1 according to the fourth embodiment, it is possible to obtain the following advantages and effects in addition to the advantages and effects (1) to (4), and (6) described above.

(9) The pet absorbent article 10 is folded in the longitudinal direction of the pet absorbent article 10 such that the top sheet 2 faces inwardly, and a portion of the first end 91 where the hook tape 8 is arranged to project upwardly beyond the second end 92. As a result, it is possible to provide the first outer face 11 including the hook tape 8 arranged on the top sheet 2. Therefore, even in the package in which the pet absorbent articles 10 having the hook tape 8 on the top sheet side are stored in the packing bag 20, it is possible to provide the absorbent article package in which the pet absorbent article 10 can be easily extracted one by one.

Figure 13:
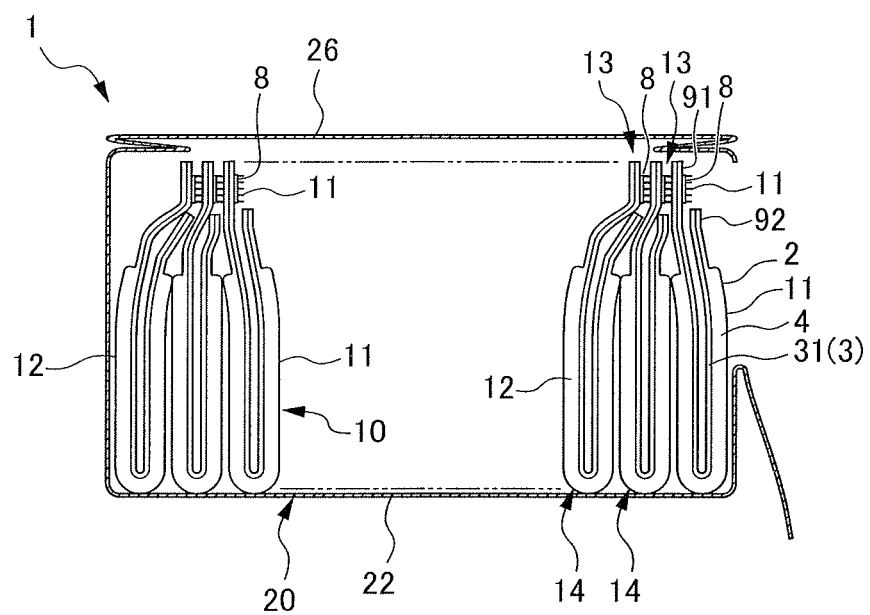
FIG. 13 is a diagram illustrating a state that a plurality of absorbent articles are stored in the packing bag of the absorbent article package according to a fifth embodiment.

Next, the absorbent article package 1 according to the fifth embodiment will be described with reference to FIG. 13. FIG. 13 is a diagram illustrating a state that a plurality of pet absorbent articles 10 are stored in the packing bag 20 of the absorbent article package according to the fifth embodiment.

The absorbent article package 1 according to the fifth embodiment is different from that according to the third embodiment in the folding of the pet absorbent article 10.

According to the fifth embodiment, the pet absorbent article 10 is folded asymmetrically in the longitudinal direction of the pet absorbent article 10 such that the back surface sheet 31 faces inwardly, and a portion of the first end 91 where the hook tape 8 is arranged projects upwardly beyond the second end 92 as shown in FIG. 13. That is, according to the fifth embodiment, the back surface sheet 31 and the hook tape 8 arranged on the back surface sheet 31 is included in the upwardly projecting first end 91 and on the first outer face 11 of the pet absorbent article 10, and the hook tape 8 is engaged with the top sheet 2 in the upwardly projecting first end 91 of the adjacent pet absorbent article 10.

In the absorbent article package 1 according to the fifth embodiment, it is possible to obtain the advantages and effects (1) to (6) described above.

Although preferable embodiments have been described hereinbefore, the present invention is not limited by the aforementioned embodiments, but may be modified in various manners.

For example, although the package 1 for storing the pet absorbent articles 10 is explained in the aforementioned embodiments, the present invention is not limited thereto. That is, a package for storing absorbent articles for human, such as disposable diapers or urine absorbent pads, may be employed in some embodiments of the present invention.

Figure 14:
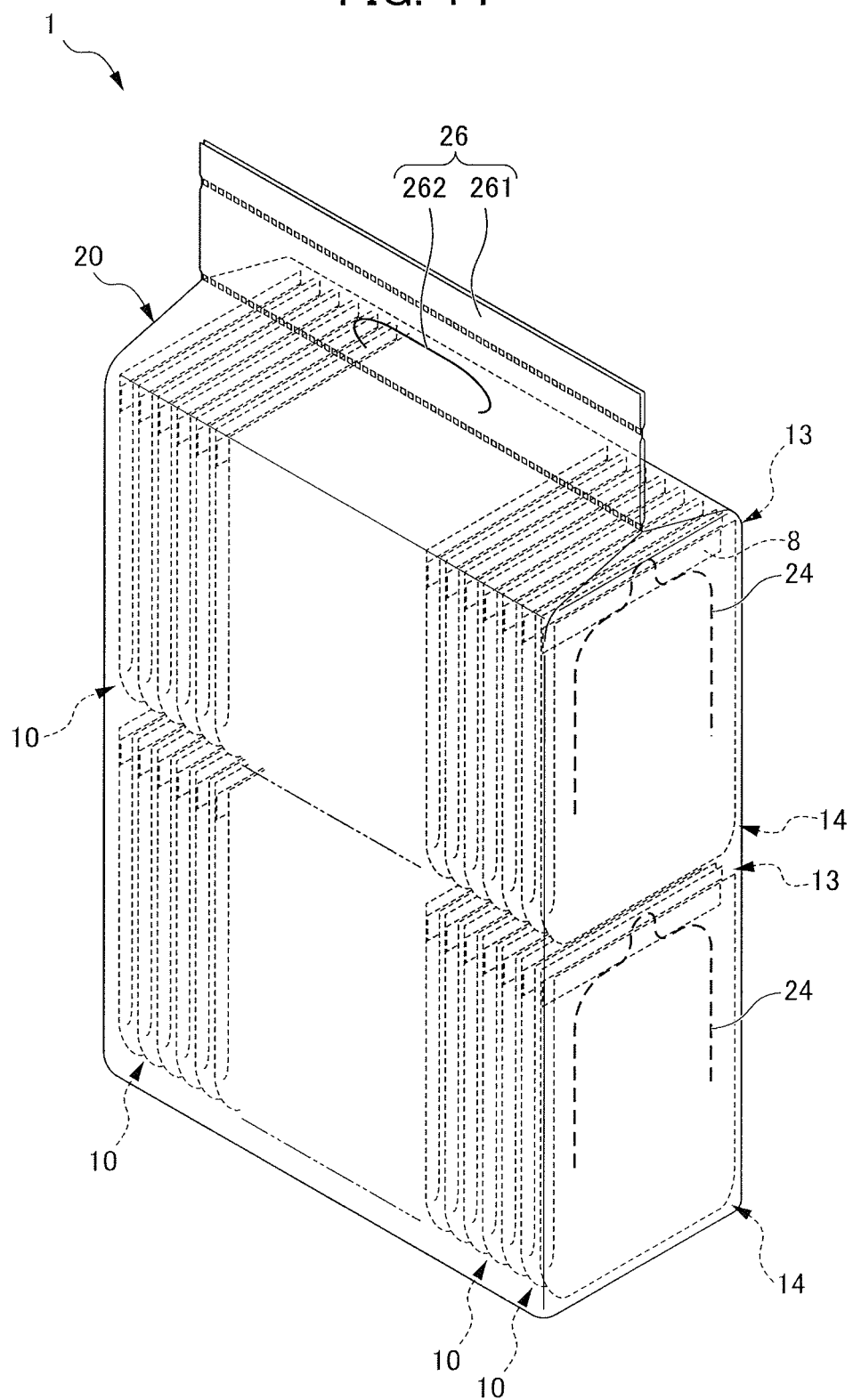
FIG. 14 is a perspective view illustrating a first modification of the absorbent article package.
Figure 15:
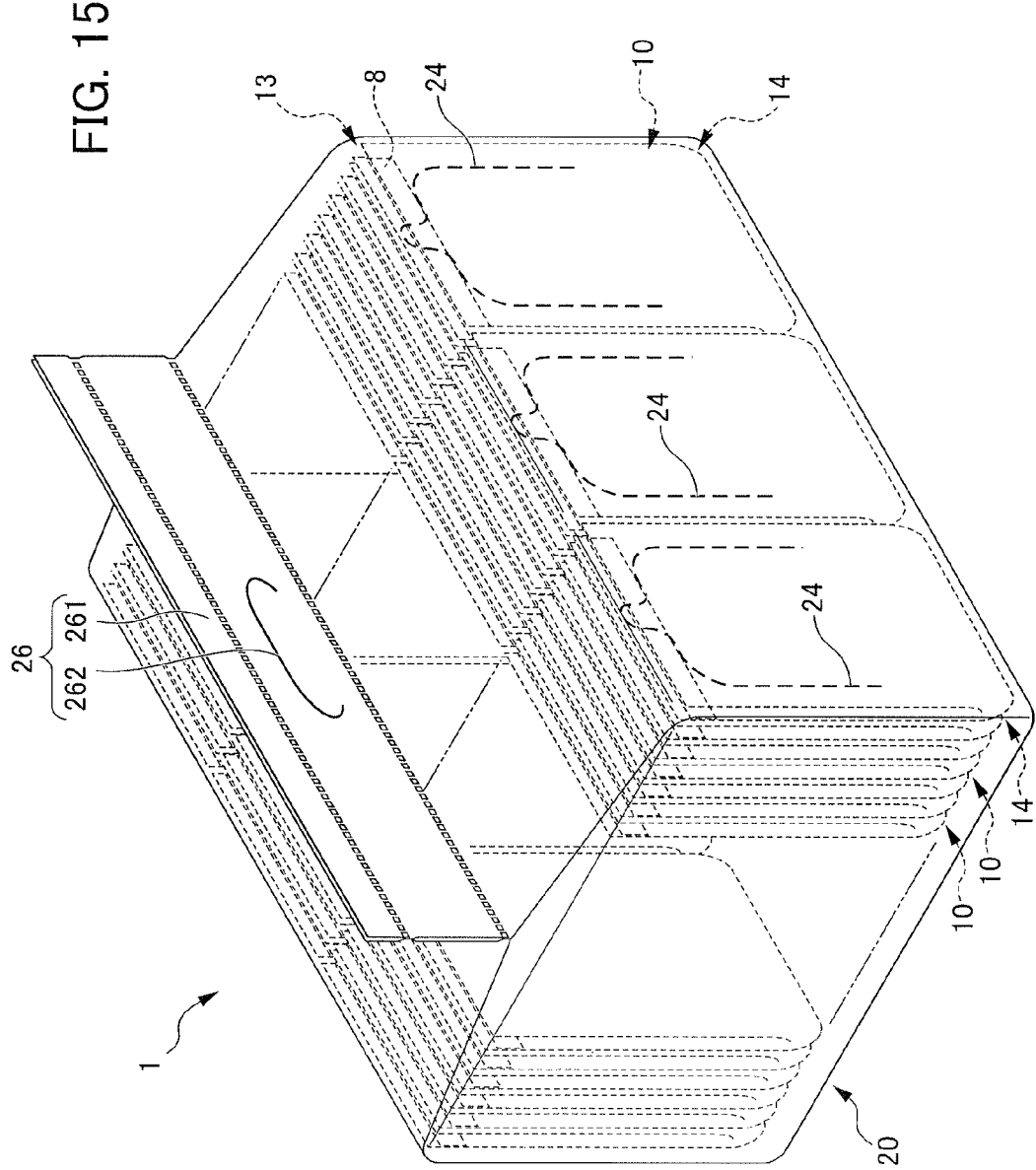
FIG. 15 is a perspective view illustrating a second modification of the absorbent article package.

Although the absorbent article package 1 in which a plurality of pet absorbent articles 10 are stored in the packing bag 20 along a line in a layered state is explained in the aforementioned embodiments, the present invention is not limited thereto. That is, a plurality of pet absorbent articles 10 may be stored in the packing bag 20 in two or more stages as shown in FIG. 14 to constitute the absorbent article package 1. Alternatively, a plurality of pet absorbent articles 10 may be stored in the packing bag 20 in a plurality of lines (for example, three lines) as shown in FIG. 15 to constitute the absorbent article package 1.

Figure 16:
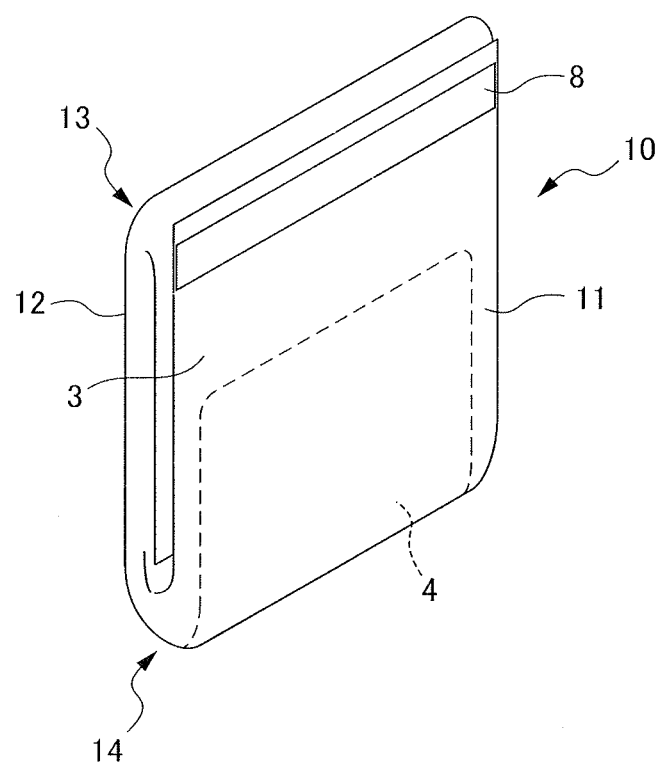
FIG. 16 is a diagram illustrating a first modification of a method of folding an absorbent article.
Figure 17:
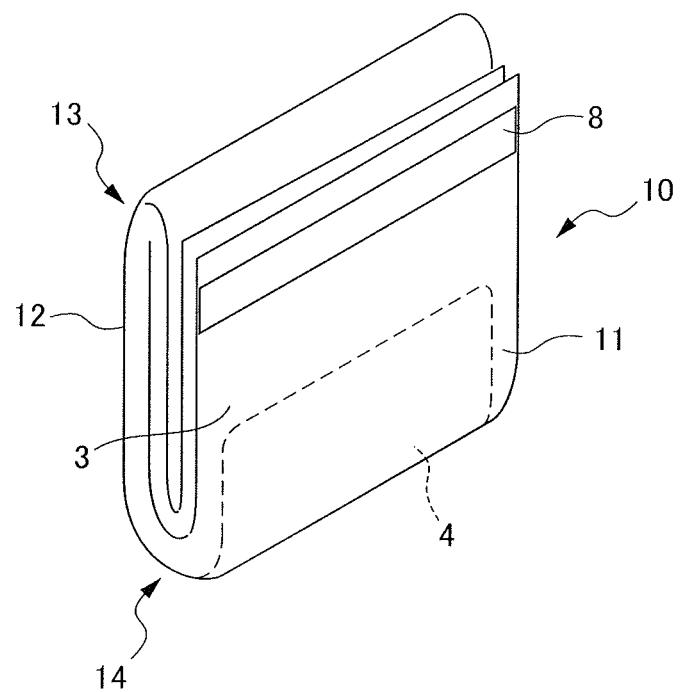
FIG. 17 is a diagram illustrating a second modification of the method of folding an absorbent article.

Although the pet absorbent articles 10 are stored in the packing bag 20 while they are folded in half in the longitudinal direction in the aforementioned embodiments, the present invention is not limited thereto. That is, the pet absorbent article 10 may be stored in the packing bag while it is three-folded in the longitudinal direction as shown in FIG. 16. Alternatively, the pet absorbent article 10 may be stored in the packing bag while it is four-folded in the longitudinal direction as shown in FIG. 17.

Figure 18A:
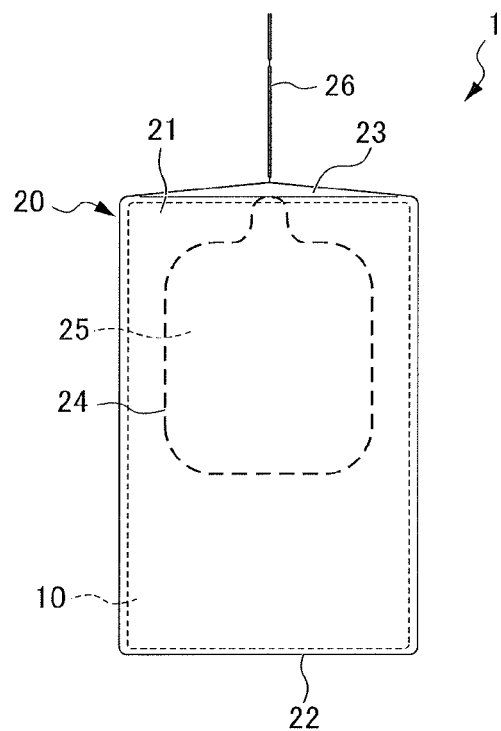
FIG. 18A is a diagram illustrating a first modification of the tearable portion shape.

In addition, the shape of the tearable portion 24 (opening 25) is not limited to the shape described above. That is, when the tearable portion 24 is formed in a ring shape to provide the opening 25 as shown in FIG. 18A, the sheet member may be separately provided. As a result, when the opening 25 is formed by tearing the tearable portion 24, it is possible to prevent the opening 25 from being formed in an excessively large size.

Figure 18B:
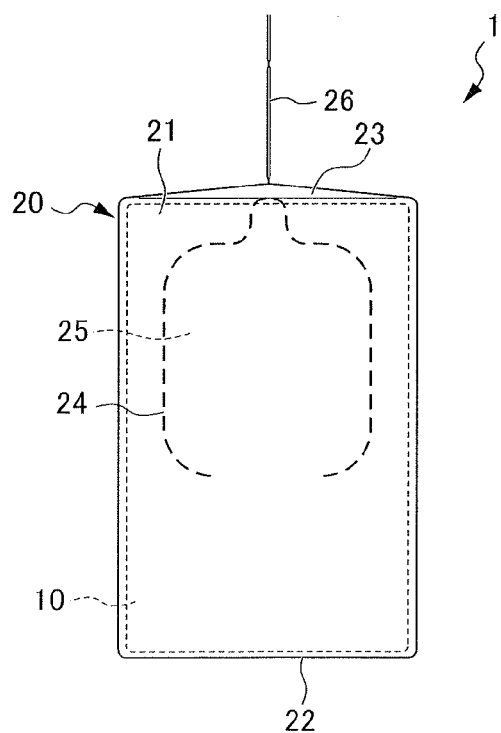
FIG. 18B is a diagram illustrating a second modification of the tearable portion shape.
Figure 18C:
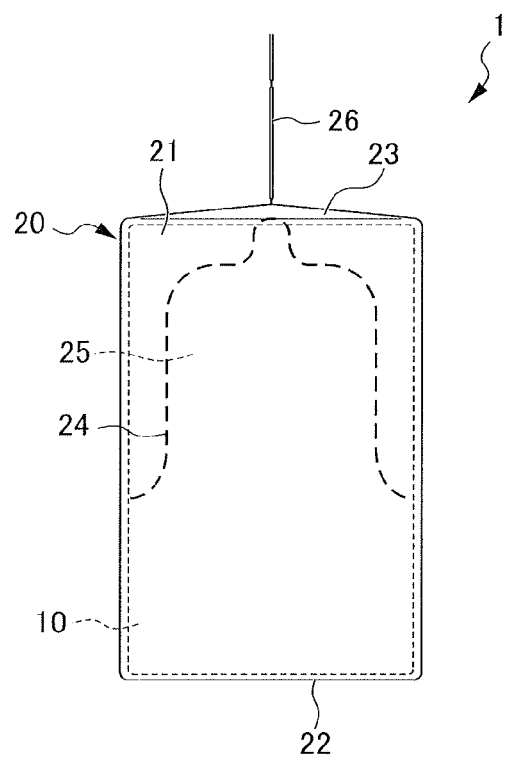
FIG. 18C is a diagram illustrating a third modification of the tearable portion shape.

In addition, as shown in FIG. 18B, the end portions of the tearable portion 24 extending toward the bottom face 22 may be directed inwardly in the width direction of the first face 21. Alternatively, as shown in FIG. 18C, the end portions of the tearable portion 24 extending toward the bottom face 22 may be directed outwardly in the width direction of the first face 21. In case the end portions of the tearable portion 24 are directed inwardly or outwardly in the width direction of the first face 21 in this manner, it is possible to prevent the opening 25 from being formed in an excessively large size when the opening 25 is formed by tearing the tearable portion 24.

Figure 19:
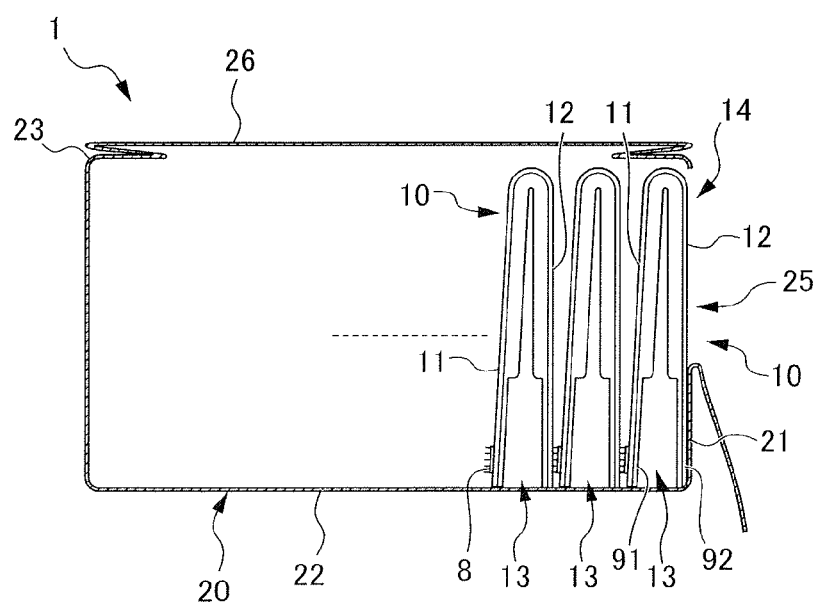
FIG. 19 is a diagram illustrating a modification of the arrangement of the absorbent articles stored in the packing bag.

Although the first end portion 13 where the hook tape 8 is provided is arranged on the top face side of the packing bag 20 in the aforementioned embodiments, the present invention is not limited thereto. That is, the first end portion 13 where the hook tape 8 is provided may be arranged on the bottom face side of the packing bag 20 as shown in FIG. 19.

In the above-described embodiments, various elements are described to have rectangular or substantially rectangular shapes; however, the present invention is not limited thereto. In other words, other shapes are contemplated in further embodiments.

In addition, the engagement member is described as a hook tape; however, the present invention is not limited thereto. In other words, other types of releasable fasteners are contemplated in further embodiments.

This application claims the benefit of Japanese Application No. 2011-124670 the entire disclosure of which is incorporated by reference herein.

The invention claimed is:

1. A package of absorbent articles for pets, said package comprising:
    a plurality of absorbent articles each adapted to be worn on a girth of a pet, and folded along a longitudinal direction thereof to define a first outer face and a second outer face; and
    a packing bag that stores the plurality of absorbent articles in a layered state such that the first outer face of each of the plurality of the absorbent articles makes contact with the second outer face of an adjacent absorbent article, wherein
    each of the absorbent articles includes
        a liquid-permeable surface layer;
        a liquid-impermeable back surface layer;
        an absorbent core arranged between the surface layer and the back surface layer; and
        an engagement member arranged on the first outer face and engaging with the second outer face of the adjacent absorbent article, the engagement member is arranged on the back surface layer and in a vicinity of a first end of the absorbent article in the longitudinal direction,
    each of the folded absorbent articles has (i) the back surface layer defining the first and second outer faces and (ii) the surface layer facing inwardly,
    the surface layer and the back surface layer include nonwoven fabrics engageable with the engagement member,
    an engaging force between the engagement member and the nonwoven fabric of the back surface layer is lower than an engaging force between the engagement member and the nonwoven fabric of the surface layer,
    the packing bag includes a first face positioned to face the first or second outer faces of the absorbent articles stored in the packing bag and configured to form therein an opening to allow the absorbent articles to be extracted,
    the nonwoven fabric of the surface layer of each of the absorbent articles is configured to be engaged with the engagement member of said absorbent article when said absorbent article is worn on a girth of a pet, and
    the nonwoven fabric of the back surface layer of said absorbent article is engaged with the engagement member of the adjacent absorbent article when said absorbent article and the adjacent absorbent article are stored in the packing bag.

2. The package according to claim 1, wherein the packing bag further includes a tearable portion formed in the first face and configured to be torn to form the opening.

3. The package according to claim 1, wherein
    each of the folded absorbent article includes a second end opposite to the first end,
    the engagement member is arranged in the vicinity of the first end on the first outer face, and
    the first face is configured to form the opening on a side where the first end is positioned and not on a side where the second end is positioned.

4. The package according to claim 1, wherein
    each of the folded absorbent article includes a second end opposite to the first end,
    the engagement member is arranged in the vicinity of the first end on the first outer face, and
    the first face is configured to form the opening on a side where the second end is positioned and not on a side where the first end is positioned.

5. The package according to claim 3, wherein the packing bag further includes:
    a top face located on a side where the first ends of the plurality of the absorbent articles stored in the packing bag are arranged, and
    a grip portion provided on the top face.

6. The package according to claim 1, wherein
    each of the folded absorbent article includes a second end opposite to the first end, and
    each of the absorbent articles is folded asymmetrically in the longitudinal direction such that the first end of the absorbent article projects upwardly beyond the second end of the absorbent article in the longitudinal direction.

7. The package according to claim 1, wherein
a length of the opening in a length direction connecting a top face and a bottom face of the packing bag is 20% to 80% of a length of the first face of the packing bag in the length direction.

8. The package according to claim 1, wherein
a width of the opening in a width direction perpendicular to a length direction connecting a top face and a bottom face of the packing bag is 50% to 90% of a width of each of the absorbent articles in the width direction, and
the longitudinal directions of the absorbent articles are oriented along the length direction connecting the top face and the bottom face of the packing bag.

9. The package according to claim 1, wherein an area of the opening is 30% to 70% of an area of the first outer face or the second outer face of each of the absorbent articles.

10. The package according to claim 1, wherein the absorbent articles include a plurality of groups of absorbent articles, said groups adjacent to each other in a direction connecting side surfaces of the packing bag.

11. The package according to claim 1, wherein the absorbent articles include a plurality of groups of absorbent articles, said groups stacked on each other in a direction connecting a top face and a bottom face of the packing bag.

12. The package according to claim 1, wherein
the engaging force between the engagement member of said absorbent article and the nonwoven fabric of the back surface layer of the adjacent absorbent article when said absorbent article and the adjacent absorbent article are stored in the packing bag is lower than the engaging force between the engagement member and the nonwoven fabric of the surface layer of said absorbent article when said absorbent article is worn on a girth of a pet.

13. The package according to claim 1, wherein
the first outer face of each of the absorbent articles is arranged closer to the first face of the packing bag than the second outer face of said absorbent article, and
the engagement member on the first outer face has a higher friction coefficient than a remainder of the first outer face.

* * * * *